(12) United States Patent
Glavicic et al.

(10) Patent No.: US 9,753,014 B2
(45) Date of Patent: Sep. 5, 2017

(54) DETECTION AND MEASUREMENT OF DEFECT SIZE AND SHAPE USING ULTRASONIC FOURIER-TRANSFORMED WAVEFORMS

(75) Inventors: Michael G. Glavicic, Indianapolis, IN (US); Jeffrey A. Gilbert, Avon, IN (US); Jason A. Gilbert, legal representative, Ione, CA (US)

(73) Assignee: Rolls-Royce Corporation, Indianapolis, IN (US)

( * ) Notice: Subject to any disclaimer, the term of this patent is extended or adjusted under 35 U.S.C. 154(b) by 760 days.

(21) Appl. No.: 14/000,054

(22) PCT Filed: Feb. 17, 2012
(Under 37 CFR 1.47)

(86) PCT No.: PCT/US2012/025660
§ 371 (c)(1),
(2), (4) Date: Oct. 24, 2013

(87) PCT Pub. No.: WO2012/112898
PCT Pub. Date: Aug. 23, 2012

(65) Prior Publication Data
US 2014/0074410 A1 Mar. 13, 2014

Related U.S. Application Data

(60) Provisional application No. 61/444,585, filed on Feb. 18, 2011.

(51) Int. Cl.
*G01N 29/11* (2006.01)
*G01N 29/04* (2006.01)
(Continued)

(52) U.S. Cl.
CPC ........... *G01N 29/11* (2013.01); *G01N 29/043* (2013.01); *G01N 29/12* (2013.01); *G01N 29/30* (2013.01);
(Continued)

(58) Field of Classification Search
None
See application file for complete search history.

(56) References Cited

U.S. PATENT DOCUMENTS 4,052,889 A  10/1977 Mucciardi et al.
5,029,475 A   7/1991 Kikuchi et al.
(Continued)

FOREIGN PATENT DOCUMENTS

EP  0485960 A2  5/1992
EP  0763732 A2  3/1997
(Continued)

OTHER PUBLICATIONS

Response to the Office Action mailed Nov. 4, 2015, from U.S. Appl. No. 13/579,770, filed Feb. 4, 2016, 20 pp.
(Continued)

*Primary Examiner* — An Do
*Assistant Examiner* — Renee I Wilson
(74) *Attorney, Agent, or Firm* — Shumaker & Sieffert, P.A.

(57) ABSTRACT

A system may include a data analysis device that is configured to receive from an ultrasonic waveform detector ultrasonic waveform data representative of an ultrasonic waveform that propagated through a sample and resonated within a defect within the sample. The data analysis device may be further configured to select a portion of the ultrasonic waveform data, apply a Fast Fourier Transform to the portion of the ultrasonic waveform data to transform the portion from a time domain to a frequency domain, identify
(Continued)

a characteristic frequency of the portion in the frequency domain, and determine a characteristic of the defect based on the characteristic frequency of the portion. In some examples, the characteristic of the defect may be at least one of an approximate size or an approximate shape of the defect.

20 Claims, 9 Drawing Sheets

(51) Int. Cl.

| | | |
|---|---|---|
| *G01N 29/12* | (2006.01) | |
| *G01N 29/44* | (2006.01) | |
| *G01N 29/46* | (2006.01) | |
| *G01N 29/30* | (2006.01) | |

(52) U.S. Cl.
CPC ......... *G01N 29/4427* (2013.01); *G01N 29/46* (2013.01); *G01N 2291/044* (2013.01); *G01N 2291/2693* (2013.01)

(56) References Cited

U.S. PATENT DOCUMENTS

| | | | |
|---|---|---|---|
| 5,402,681 A | 4/1995 | Nakaso et al. | |
| 6,057,927 A | 5/2000 | Levesque et al. | |
| 6,128,092 A * | 10/2000 | Levesque ............ | G01N 29/069 356/451 |
| 6,401,537 B1 | 6/2002 | Gigliotti, Jr. et al. | |
| 2003/0130803 A1 | 7/2003 | Chou et al. | |
| 2006/0062438 A1 | 3/2006 | Rowe | |
| 2007/0006651 A1 | 1/2007 | Kruger et al. | |
| 2010/0148627 A1 | 6/2010 | Funasaka et al. | |
| 2013/0039147 A1 | 2/2013 | Witte et al. | |
| 2014/0074410 A1 | 3/2014 | Glavicic et al. | |

FOREIGN PATENT DOCUMENTS

| | | |
|---|---|---|
| GB | 2254426 A | 10/1992 |
| JP | 2005251485 A | 9/2005 |
| JP | 2009097972 A | 5/2009 |
| WO | 2012112898 A1 | 8/2012 |

OTHER PUBLICATIONS

Dixon et al., "The accuracy of acoustic birefringence shear wave measurements in sheet metal," Journal of Applied Physics, vol. 104, No. 11, pp. 114901-1-114901-5, Dec. 2, 2008.
Anderson et al., "Ultrasonic Measurement of the Kearns Texture Factors in Zircaloy, Zirconium, and Titanium," Metallurgical and Materials Transactions, vol. 30, No. 8, Aug. 1, 1999, pp. 1981-1988.
Moreau et al., "On-line measurement of texture, thickness and plastic strain ratio using laser-ultrasound resonance spectroscopy," Ultrasonics, IPC Science and Technology Press Ltd., vol. 40, No. 10, pp. 1047-1056, Dec. 1, 2002.
U.S. Appl. No. 13/579,770, by Michael G. Glavicic, et al., filed Dec. 20, 2012.
International Search Report and Written Opinion of international application No. PCT/US2012/025660, dated May 23, 2013, 5 pp.
International Preliminary Report on Patentability from corresponding international application No. PCT/US2012/025660, dated Aug. 21, 2013, 7 pp.
Office Action from U.S. Appl. No. 13/579,770, dated Sep. 16, 2016, 25 pp.
Amendment in Response to Office Action mailed Sep. 16, 2016, from U.S. Appl. No. 13/579,770, filed Dec. 16, 2016, 19 pp.
Kundu et al., Crystallographic Texture of Stress-Affected Bainite, The Royal Society, Jul. 4, 2007, 20 pp.
Final Office Action from U.S. Appl. No. 13/579,770, dated Apr. 28, 2016, 28 pp.
Response to Office Action mailed Apr. 28, 2016, from U.S. Appl. No. 13/579,770, filed Jul. 28, 2016,18 pp.
Office Action from U.S. Appl. No. 13/579,770, dated Nov. 4, 2015, 18 pp.
Final Office Action from U.S. Appl. No. 13/579,770, dated Mar. 29, 2017, 10 pp.
Amendment in Response to Office Action dated Mar. 29, 2017, from U.S. Appl. No. 13/579,770, filed May 30, 2017, 14 pp.
Advisory Action from U.S. Appl. No. 13/579,770, dated Jun. 21, 2017, 4 pp.

* cited by examiner

DETECTION AND MEASUREMENT OF DEFECT SIZE AND SHAPE USING ULTRASONIC FOURIER-TRANSFORMED WAVEFORMS

CROSS REFERENCE TO RELATED APPLICATIONS

This application is a national stage entry under 35 U.S.C. §371 of PCT Application No. PCT/US2012/025660, filed Feb. 17, 2012, which claims the benefit of U.S. Provisional Application No. 61/444,585, filed Feb. 18, 2011. The entire contents of PCT Application No. PCT/US2012/025660 and U.S. Provisional Application No. 61/444,585 are incorporated herein by reference.

TECHNICAL FIELD

The disclosure is directed to systems and techniques for utilizing ultrasonic waveforms to detect defects in a material.

BACKGROUND

Components of high-temperature mechanical systems, such as gas-turbine engines, operate in severe environments. Some components may be formed of a metal or metal alloy, such as, for example, titanium or a titanium alloy. Other components may be formed of a ceramic or a composite material.

Mechanical properties of a material may depend at least in part on the microstructure of the material, including a presence or absence of defects, such as holes, voids or sections with a different chemical composition or phase constitution, within the material. For this reason, knowledge of the presence or absence of defects in the material may be desired before utilizing the material in a component, such as a gas turbine engine component.

SUMMARY

Systems and techniques may use ultrasonic energy to detect a defect within a material. The systems and techniques may additionally allow determination of an approximate location of the defect within the material, an approximate size of the defect, and/or an approximate shape of the defect based on a characteristic of the ultrasonic energy. In some examples, the material may comprise a metal, an alloy, a ceramic, composite material, or the like. More particularly, disclosed herein are techniques for detecting a defect and measuring a size and/or shape of the defect using Fast Fourier Transforms (FFT) of sensed ultrasonic waveforms. In some examples, the defect is a void or hole in the material, while in other examples, the defect may be a section of the material with a different chemical composition or phase constitution that a neighboring portion of the material.

In some examples, an ultrasonic waveform generator (e.g., a transducer) may generate an ultrasonic waveform and transmit the waveform into a first surface of a sample of a material, through which the ultrasonic waveform propagates. At least a portion of the waveform may encounter a defect, and may resonate within the defect. An ultrasonic waveform detector (e.g., the transducer) senses the resonated ultrasonic waveform. The ultrasonic waveform detector measures the resonated ultrasonic waveform (e.g., amplitude and/or frequency) as a function of time and transmits the measured data to a data analysis device.

The data analysis device may mathematically manipulate the measured data to select a portion of the data, either automatically or in response to a user input. In some examples, the data analysis device may divide a sub-set of the measured data into one or more portions and may sequentially select the one or more portions of the data. In other examples, the data analysis device may divide substantially all of the measured data into a plurality of portions and may sequentially select the portions of the data. Each of the one or more portions includes a plurality of time values and associated amplitudes and/or frequencies of the ultrasonic waveform. The portions may be representative of a position (e.g., depth) within the sample based on a time delay from generation of the waveform or initial sensing of the waveform to sensing of the waveform portion corresponding to the selected portion of data.

The data analysis device may apply a FFT to the selected portion of data to transform the data from the time domain to the frequency domain, and may identify a characteristic frequency of the data, such as a central, dominant, or other harmonic frequency, for the selected portion. The data analysis device may utilize the characteristic frequency of the waveform for the selected portion to determine whether the selected portion of measured data includes a defect. Additionally and optionally, the data analysis device may use the characteristic frequency to determine an approximate size and/or shape of the defect. In some examples, the data analysis device compares the characteristic frequency to at least one calibration curve to determine the size and/or shape of the defect. The calibration curve may be generated by subjecting samples with defects of a known size and shape to an ultrasonic waveform and determining the characteristic frequency at which the defect of known size and shape resonates. In other examples, the data analysis device may determine an approximate size of the defect by utilizing the characteristic frequency in one or more equations that relate the characteristic frequency to a dimension of a defect.

In one aspect, the disclosure is directed to a system that includes a data analysis device configured to receive from an ultrasonic waveform detector ultrasonic waveform data representative of an ultrasonic waveform that propagated through a sample and resonated within a defect within the sample. According to this aspect of the disclosure, the data analysis is configured to select a portion of the ultrasonic waveform data and apply a Fast Fourier Transform to the portion of the ultrasonic waveform data to transform the portion from a time domain to a frequency domain. The data analysis device also may be configured to identify a characteristic frequency of the portion in the frequency domain and determine a characteristic of the defect based on the characteristic frequency of the portion.

In another aspect, the disclosure is directed to a method that includes receiving from an ultrasonic waveform detector ultrasonic waveform data representative of an ultrasonic waveform that propagated through a sample and resonated within a defect within the sample. According to this aspect of the disclosure, the method further includes selecting a portion of the ultrasonic waveform data and applying a Fast Fourier Transform to the portion of the ultrasonic waveform data to transform the portion from a time domain to a frequency domain. Additionally, the method may include identifying a characteristic frequency of the portion in the frequency domain and determining a characteristic of the defect based on the characteristic frequency of the portion.

In further aspect, the disclosure is directed to a computer readable medium comprising instructions that cause a programmable processor to receive from an ultrasonic waveform detector ultrasonic waveform data representative of an ultrasonic waveform that propagated through a sample and resonated within a defect within the sample. According to this aspect of the disclosure, the computer readable additionally includes instructions that cause the programmable processor to select a portion of the ultrasonic waveform data and apply a Fast Fourier Transform to the portion of the ultrasonic waveform data to transform the portion from a time domain to a frequency domain. Further, the computer readable additionally may include instructions that cause the programmable processor to identify a characteristic frequency of the portion in the frequency domain and determine a characteristic of the defect based on the characteristic frequency of the portion. In some examples, the computer-readable medium is non-transitory.

In another aspect, the disclosure is directed to a computer readable storage medium, which may be an article of manufacture. The computer readable storage medium comprises computer readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. The computer-readable medium may be non-transitory.

The details of one or more examples are set forth in the accompanying drawings and the description below. Other features, objects, and advantages will be apparent from the description and drawings, and from the claims.

DETAILED DESCRIPTION

In general, the present disclosure is directed to techniques for detecting a defect in a material and, optionally, measuring an approximate size and/or shape of the defect, using ultrasonic energy.

Figure 1:
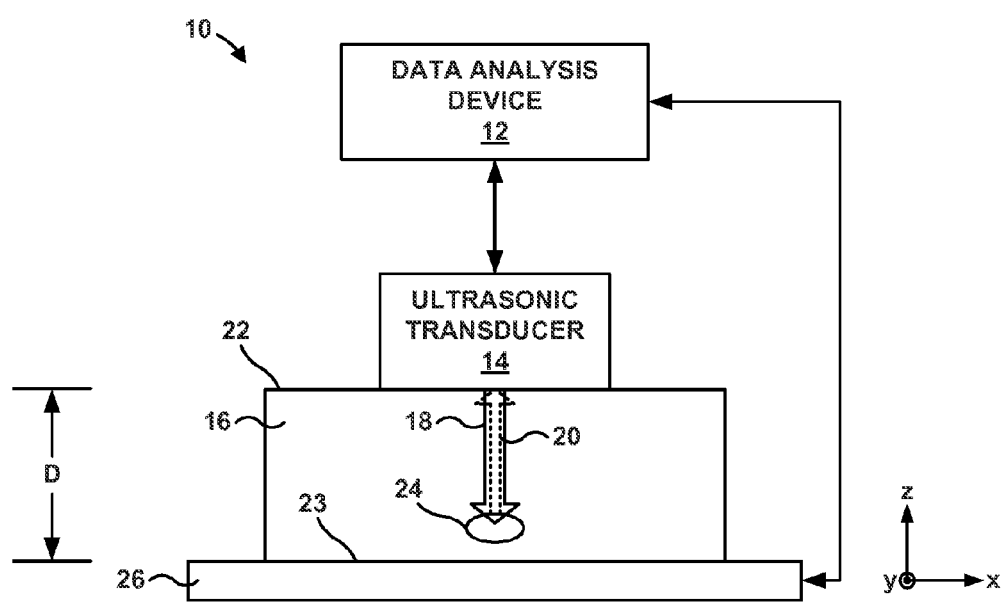
FIG. 1 is a block diagram of an example system for performing an ultrasonic measurement to detect and, optionally, measure a defect within a material.

FIG. 1 is a schematic diagram illustrating an example of a system 10 that may be used to detect a defect within sample 16. System 10 includes a data analysis device 12, an ultrasonic transducer 14, and a stage 26. Sample 16 is coupled to stage 26, and ultrasonic transducer 14 is in contact with a first surface 22 of sample 16.

Sample 16 may be any material, including, for example, a ceramic, a metal or a metal alloy, or a composite material. For example, sample 16 may include an alloy used in a high temperature mechanical system, such as a gas turbine engine. Such alloys include titanium-based, nickel-based, magnesium-based or zirconium-based superalloys. In other examples, sample 16 may include a ceramic or ceramic matrix composite (CMC). The ceramic may be a silicon-containing ceramic, such as silica ($SiO_2$), silicon carbide (SiC) or silicon nitride ($Si_3N_4$); alumina ($Al_2O_3$); aluminosilicate; or the like. CMCs may include a matrix material and a reinforcement material. In some examples, the matrix material and the reinforcement material may have similar compositions, such as an SiC matrix material and an SiC reinforcement material. In other examples, the matrix material and the reinforcement material may have different compositions, such as aluminosilicate reinforcement material in an alumina matrix material. Other composite materials may include, for example, carbon-fiber reinforced polymers, which may include a carbon-fiber reinforcement material in a polymer matrix material, such as an epoxy.

In some examples, a material that includes defects may be disfavored. For example, defects may affect properties of the material, and the presence of a defect, a certain number of defects, or defects in a certain location may render a material unsuitable for particular applications.

Figure 2:
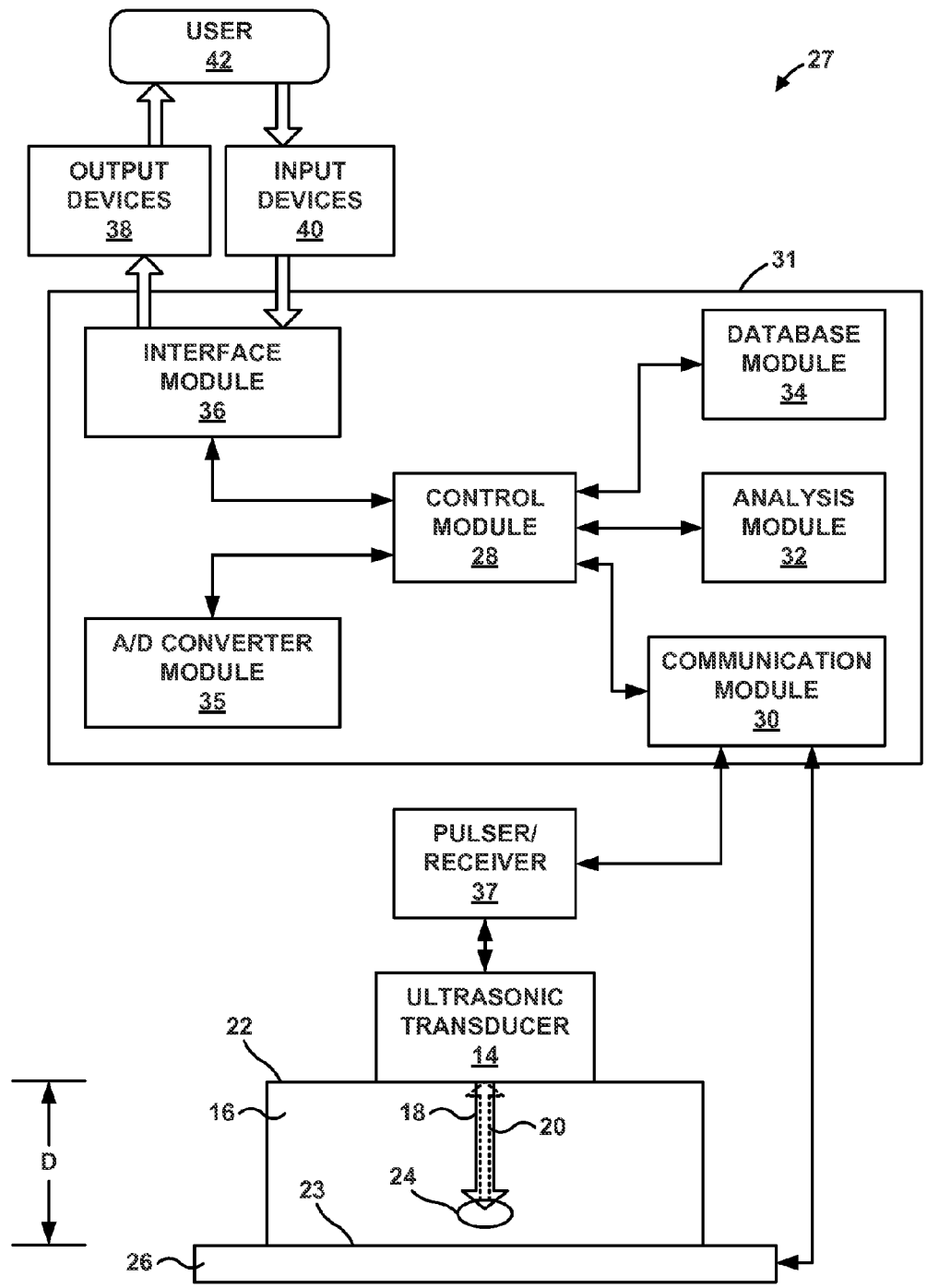
FIG. 2 is a functional block diagram illustrating an example of a system for performing an ultrasonic measurement to detect and, optionally, measure a defect within a material.
Figure 3:
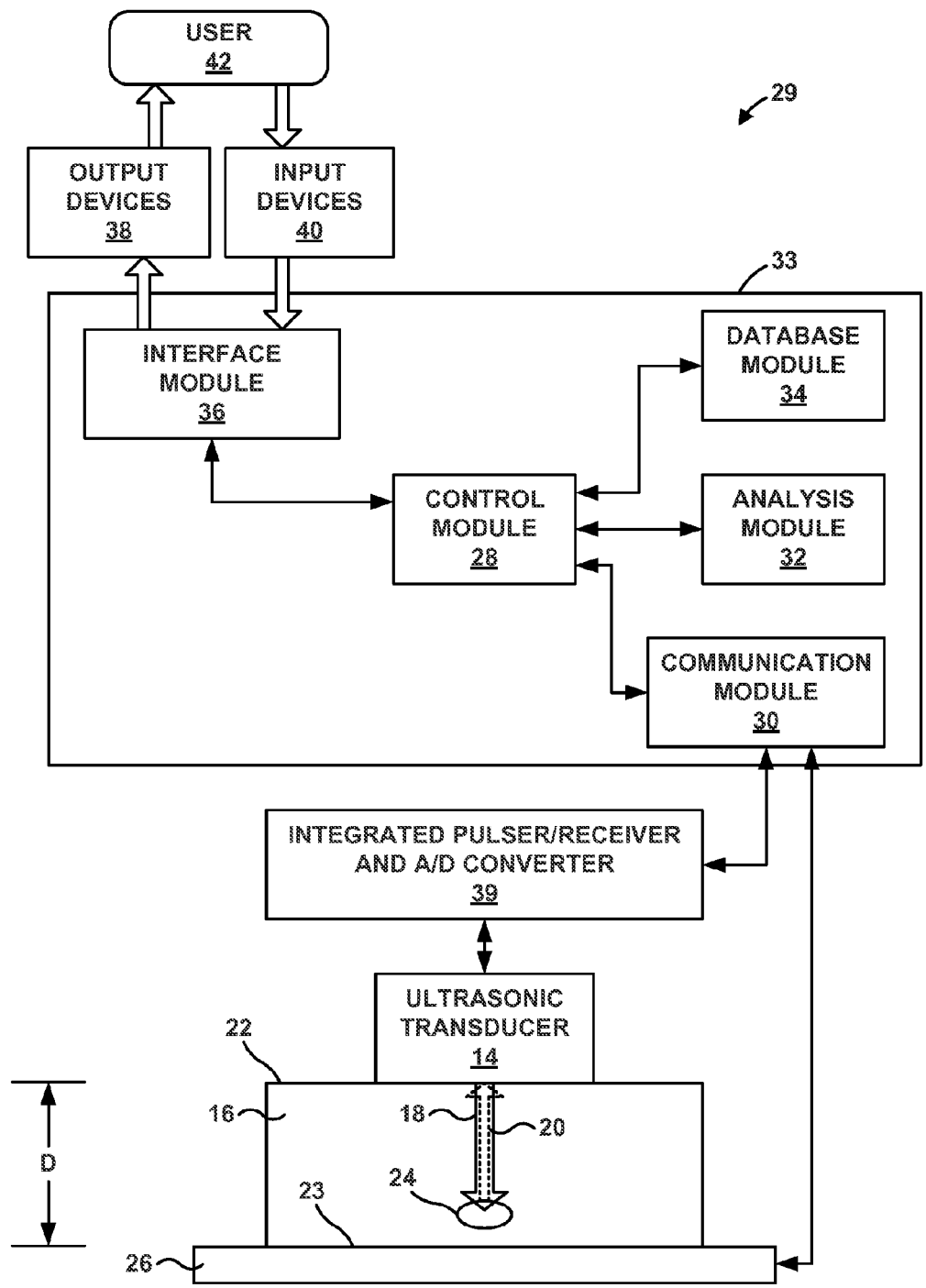
FIG. 3 is a functional block diagram illustrating another example of a system for performing an ultrasonic measurement to detect and, optionally, measure a defect within a material.

System 10 may be utilized to detect the presence of one or more defects within sample 16. In some examples, system 10 may allow determination of the approximate size and/or shape of the defect, and may additionally or alternatively facilitate determination of an approximate location of the defect within sample 16. System 10 includes data analysis device 12, which controls operation of system 10 automatically or under control of a user 40 (FIGS. 2 and 3).

Data analysis device 12 may be a general-purpose workstation, desktop computer, laptop computer, a handheld computing device, a personal digital assistant (PDA), or other computing device. Data analysis device 12 may include a microprocessor, digital signal processor (DSP), field programmable gate array (FPGA), application specific integrated circuit (ASIC) or other hardware, firmware and/or software for implementing the techniques described in this disclosure. In other words, the control of system 10 and analysis of ultrasonic waveform data, as described herein, may be implemented in hardware, software, firmware, combinations thereof, or the like. If implemented in software, a computer-readable medium may store instructions, i.e., program code, that can be executed by a processor or DSP to carry out one or more of the techniques described herein. For example, the computer-readable medium may comprise magnetic media, optical media, random access memory (RAM), read-only memory (ROM), non-volatile random access memory (NVRAM), electrically erasable programmable read-only memory (EEPROM), magnetoresistive random access memory (MRAM), flash memory, or other media suitable for storing program code.

Data analysis device 12 controls operation of ultrasonic transducer 14 and stage 26 and receives from ultrasonic transducer 14 signals representative of the ultrasonic waveforms detected by transducer 14. Ultrasonic transducer 14 may include both a component for generating an ultrasonic waveform (a "waveform generator") and a component for detecting an ultrasonic waveform (a "waveform detector"). In some examples, at least one of the waveform generator and the waveform detector comprises a piezoelectric crystal. When exposed to a voltage pulse, a piezoelectric ultrasonic waveform generator converts the voltage pulse into mechanical energy that travels through sample 16 as a longitudinal wave. Conversely, when exposed to mechanical energy in the form of a longitudinal wave, a piezoelectric ultrasonic waveform detector converts the mechanical energy of the wave into an analog voltage signal. In some examples, a single piezoelectric crystal may be used for both the waveform generator and the waveform detector, while in other examples, a first piezoelectric crystal is used as the waveform generator and a second piezoelectric crystal is used as the waveform detector. In some examples, another type of ultrasonic transducer may be used, such as, for example, an electromagnetic acoustic transducer (EMAT). Although not illustrated in FIG. 1, in some examples, system 10 may include an ultrasonic waveform generator that is physically separate from the ultrasonic waveform detector instead of an integrated ultrasonic transducer 14.

Stage 26 is configured to couple to sample 16 to position and restrain sample 16 relative to ultrasonic transducer 14. In some examples, stage 26 may be configured to translate and/or rotate in at least one dimension.

In some examples, stage 26 and ultrasonic transducer 14 may be configured to operate in conjunction to position sample 16 relative to transducer 14. For example, stage 26 may be configured to translate in two dimensions (e.g., an x-y plane in the coordinate system shown in FIG. 1) and ultrasonic transducer 14 may be configured to translate in at least one dimension (e.g., the z-axis in FIG. 1). In other examples, each of ultrasonic transducer 14 and stage 26 may be configured to translate in three dimensions and may be configured to work in conjunction to position transducer 14 relative to sample 16. For example, stage 26 may be configured to provide relatively coarse positioning of sample 16, while ultrasonic transducer 14 may be configured to provide relatively more precise positioning. As another example, stage 26 may be configured to provide relatively slow positioning of sample 16 relative to transducer 14, while transducer 14 may be configured to provide relatively faster positioning with respect to sample 16. In some examples, one or both of ultrasonic transducer 14 or stage 26 may be configured to move according to another coordinate system. For example, one or both of ultrasonic transducer 14 or stage 26 may be configured to be positioned according to a polar coordinate system or a spherical coordinate system. In other words, positioning of one or both of ultrasonic transducer 14 or stage 26 may include rotational positioning and not only linear positioning.

Once ultrasonic transducer 14 is positioned relative to sample 16 such that transducer 14 contacts a first surface 22 of sample 16 either directly or via an interface fluid, a processor of data analysis device 12 may control the ultrasonic waveform generator in transducer 14 to generate an ultrasonic waveform 18. Ultrasonic transducer 14 may be configured to direct at least a portion of ultrasonic waveform 18 into sample 16 through first surface 22. Ultrasonic waveform 18 may comprise a frequency between, for example, approximately 2.5 megahertz (MHz) and approximately 15 MHz, such as, for example, approximately 5 MHz. In some examples, waveform 18 may comprise a frequency greater than 15 MHz or less than 2.5 MHz. In some examples, the frequency of ultrasonic waveform 18 may influence the depth to which sample 16 is interrogated.

Ultrasonic waveform 18 propagates through sample 16 from first surface 22 toward second surface 23. In some examples, at least a portion of ultrasonic waveform 18 may resonate within a defect 24 positioned within sample 16 that has a different acoustic impedance from surrounding material in sample 16. For example, ultrasonic waveform 18 may encounter a resonator, such as a void, hole, or a portion of sample 16 that has a different chemical composition or phase constitution, within which a portion of waveform 18 resonates to form a resonated ultrasonic waveform 20. At least a portion of resonated ultrasonic waveform 20 propagates back through sample 16 to first surface 22.

At first surface 22, the waveform detector in ultrasonic transducer 14 senses resonated ultrasonic waveform 20. As described above, in some examples, the waveform detector is the same physical component as the waveform generator (e.g., a single piezoelectric crystal), while in other examples, the waveform detector may be a separate physical component from the waveform generator (e.g., the generator and detector may be separate piezoelectric crystals). The waveform detector in ultrasonic transducer 14 may be configured to sense resonated ultrasonic waveform 20 as an analog signal, in which the amplitude or frequency or both of resonated waveform 20 are measured as a function of time. For example, a piezoelectric waveform detector may generate an analog voltage signal in response to mechanical energy propagating through sample 16 as waveform 20.

The analog signal may be digitized by an analog-to-digital (A/D) converter (not shown in FIG. 1) and transmitted to data analysis device 12. The A/D converter may sample the analog signal at a predetermined sampling rate, and the sampling rate determines the time duration represented by each data bit. The sampling rate used by the A/D converter may be greater than the Nyquist rate (twice the maximum component frequency of the signal). Beyond this rate, an increased sampling rate may facilitate greater accuracy in detecting and, optionally, measuring a size and/or shape of defect 24, but may result in more data, with correspondingly higher computational and data storage costs.

The A/D converter may digitize the analog signal at a specific bit depth. The bit depth defines the number of discrete values that can be used to represent the amplitude of the analog signal for a given time value. An increased bit depth results in finer distinctions between adjacent amplitude values and leads to greater fidelity of the digitized signal to the analog signal. In some examples, the A/D converter may digitize the analog signal at a bit depth of at least 8 bits. For example, the A/D converter may be an 8-bit, 10-bit, 12-bit, 14-bit, or 16-bit A/D converter.

The digitized data is representative of the ultrasonic waveform data sensed by the waveform detector in ultrasonic transducer 14. The digitized data may comprise an array or matrix in which a first column or row stores sequential time values, a second column or row stores sequential amplitudes values associated with the respective time values, and a third column or row stores sequential frequency values associated with the respective time values. As described above, the granularity (e.g., the resolution of time values or spacing between adjacent time values) of the digitized data is a function of the sampling rate, which may be predetermined and stored in a memory of data analysis device 12, or may be input by a user.

A processor of data analysis device 12 then manipulates the digitized signal representative of resonated ultrasonic waveform 20 (hereafter "the digital signal") to extract a characteristic frequency of resonated ultrasonic waveform 20 for a selected portion of the waveform 20. The processor of data analysis device 12 first selects a portion of the digital signal, which comprises a plurality of sequential time values and the associated amplitude and/or frequency values. The plurality of time values may be labeled $t_j$, where j runs from p to q, and (q−p+1) is the number of time values in the selected portion. Because resonated ultrasonic waveform 20 is sensed as a function of time, the sensed data at a given time corresponds to data for a certain depth from first surface 22 in sample 16. In some examples, the position as a function of time may be converted into an approximate physical position within sample 16 using an average velocity of resonated ultrasonic waveform 20 and a time of flight of the ultrasonic waveform 18 and resonated ultrasonic waveform 20. In this way, by selecting a portion of the digital signal corresponding to a plurality of sequential time values and processing this portion of the digital signal according to techniques described herein, data analysis device 12 may determine a presence and, optionally an approximate size and/or shape, of defect 24 with respect to position within sample 16.

To detect a presence of defect 24 and, optionally, determine a size and/or shape of defect 24, a processor of data analysis device 12 may apply a fast Fourier Transform (FFT) to the selected portion of the digital signal to transform the data from the time domain to the frequency domain. The transformed portion of the digital signal may include a characteristic frequency, which the processor of data analysis device 12 may identify. In some examples, the characteristic frequency may be a central or dominant frequency of the transformed data. In other examples, the characteristic frequency may be another harmonic frequency of the transformed data. The processor of data analysis device 12 then may utilize the characteristic frequency to determine whether defect 24 is present in sample 16 and, optionally, to determine a size and/or shape of defect 24, if present.

In some examples, the processor of data analysis device 12 may select a plurality of portions of the digital signal and determine a characteristic frequency for each of the plurality of portions. In some implementations, the plurality of portions may comprise contiguous, sequential portions of the digital signal, such that the processor of data analysis device 12 divides the substantially the entire digital signal into a plurality of portions. In other examples, the plurality of portions may not be contiguous, such that the processor divides less than the entire digital signal into a plurality of portions, e.g., with one or more unselected time values between the selected portions of the digital signal.

When the processor of data analysis device 12 has determined a characteristic frequency for a portion of the digital signal, the processor may store in a memory of data analysis device 12 the characteristic frequency with an index or value representing the selected portion. In some examples, the processor of data analysis device 12 may store the characteristic frequencies in the memory after determining the characteristic frequency for each of a plurality of portions of the digital signal. In other examples, the processor of data analysis device 12 may store the characteristic frequency in the memory after determining the characteristic frequency for a single portion of the digital signal or some, but less than all, of the plurality of portions of the digital signal.

In some examples, the processor of data analysis device 12 may cause the characteristic frequencies and the index or value of the associated portions of the digital signal to be displayed to a user, e.g., using an output device, such as a monitor. For example, the processor of data analysis device 12 may cause the characteristic frequencies and associated index or value to be output in table format, a bar or line graph, a false color map, or the like. The user may then analyze the data and select a section of the data (e.g., at least one portion of the digital signal) that the user determines may indicate a presence of defect 24.

In other examples, the processor of data analysis device 12 may automatically detect a presence of defect 24 based on a comparison of the characteristic frequencies for at least two of the plurality of portions of the digital signal. For example, the processor of data analysis device 12 may compare the characteristic frequency of a selected portion to a characteristic frequency of at least one previously selected portion. In some implementations, the previously selected portion and the currently selected portion may be sequential portions of the digital signal, which may represent adjacent sections of sample 16. In comparing the characteristic frequencies, the processor of data analysis device 12 may determine a difference between the two characteristic frequencies. When the difference is less than a predetermined threshold value, the processor of data analysis device 12 may determine that the two characteristic frequencies indicate that the two portions of the digital signal represent a similar characteristic, e.g., both represent material with no defect or both represent a defect. In contrast, when the difference is greater than the predetermined threshold value, the processor of data analysis device 12 may determine that the two characteristic frequencies indicate that the two portions of the digital signal represent different characteristics, e.g., one represents material with no defect and one represents a defect.

In some examples, the processor of data analysis device 12 may determine a characteristic frequency or a range of characteristic frequencies that represent material with no defect based on a characteristic frequency or characteristic frequency range of a section of sample 16 (represented by one or more portions of the digital signal) that is known to not include a defect 24, such as, for example, a section of sample 16 that is near first surface 22. The processor of data analysis device 12 may then determine whether the selected portion represents a presence of a defect or material with no defect based on whether the characteristic frequency of the selected portion is similar to the characteristic frequency or characteristic frequency range of the section of sample 16 that is known to not include a defect 24. The processor of data analysis device 12 may determine whether the selected portion represents defect 24 based on at least one of the comparison between the characteristic frequencies of the two portions of the digital signal and the comparison of the characteristic frequency of the currently selected portion and the characteristic frequency or characteristic frequency range of the section of sample 16 that is known to not include a defect 24.

In some examples, instead of comparing two sequential characteristic frequencies, the processor of data analysis device 12 may compare a characteristic frequency of a selected portion of the digital signal against a mean or median characteristic frequency of a predetermined number of previously selected portions. For example, the processor of data analysis device 12 may determine a running mean of the characteristic frequencies of at least two previously selected portions and may compare the characteristic frequency of the selected portion to the running mean characteristic frequency to determine a difference value. The processor may compare this computed difference value to a threshold value to determine whether the difference value indicates a transition from one type of material to a second type of material (e.g., from defect 24 to a non-defect or from a non-defect to defect 24). In some examples, the use of a running mean or median characteristic frequency may mitigate the effect of noise in the digital signal on the detection of defect 24.

While the above techniques have been described with reference to a digital signal collected with ultrasonic transducer 14 positioned at a single location on first surface 22, in some examples, the techniques may be implemented for a plurality of positions of ultrasonic transducer 14 on first surface 22 or another surface of sample 16. As described below with respect to FIG. 5, this may allow data analysis device 12 to generate a two-dimensional or three-dimensional representation of the characteristic frequency of portions of the digital signal as a function of position within sample 16. In some examples, this may permit data analysis device 12 to determine, automatically or under control of a user, a presence of defect 24 within sample 16, a position of defect 24 within sample 16, an approximate size of defect 24, and/or an approximate shape of defect 24.

Regardless of whether the processor of data analysis device 12 detects a presence of defect 24 automatically or based on an input from a user, data analysis device may utilize the characteristic frequency of the portion of the digital signal that represents defect 24 to determine an approximate size and/or shape of defect 24. In some examples, the processor of data analysis device 12 may determine the approximate size and/or shape based on a characteristic frequency of a single portion of the digital signal, while in other examples, the processor of data analysis device 12 may first determine a mean or median characteristic frequency of multiple portions of the digital signal that have been determined to represent a single defect 24. The multiple portions of the digital signal may be indicated or selected by a user, or may be determined automatically by the processor based on the algorithm described above.

In some examples, the processor of data analysis device 12 may determine the approximate size of defect 24 based on the characteristic frequency and at least one equation for relating the characteristic frequency to a size metric, which may include, for example, a volume, diameter, or other characteristic dimension of defect 24. For example, resonators having different shapes have different equations that relate the resonant frequency to the diameter or volume of the resonator. As defect 24 may act as a resonator, equations for resonators may be used to approximately relate the characteristic frequency to the volume or diameter of the resonator, if the shape of defect 24 is known or can be assumed. If the shape of defect 24 is not known and the user does not wish to assume a shape, the characteristic frequency may be utilized in multiple equations for different shapes of resonators to give a range of approximate sizes of defect 24. Examples of equations relating frequency to size for different resonators are described below with respect to FIGS. 6, 7, and 12.

In other examples, the processor of data analysis device 12 may determine the approximate size and/or shape of defect 24 by comparing the characteristic frequency of the portion or portions corresponding to defect 24 to a calibration curve constructed based on characteristic frequencies measured from defects of known sizes and shapes. In some examples, multiple calibration curves may be generated, one calibration curve for each shape of defect 24. The approximate size and shape of defect 24 may then be determined by comparing the characteristic frequency of the portion or portions corresponding to defect 24 to each of the one or more calibration curves, determining which calibration curve best fits the characteristic frequency of the portion or portions, and determining the approximate size from the calibration curve. Examples of calibration curves for different defect shapes are described below with respect to FIG. 12. Further details of techniques that system 10 may utilize to determine a presence of defect 24, an approximate size of defect 24, and/or an approximate shape of defect are described with respect to FIGS. 4-8.

FIG. 2 is a functional block diagram of an example of a system 27, which may be used to perform an ultrasonic measurement for detecting a defect 24 in sample 26. In the example illustrated in FIG. 2, system 27 includes ultrasonic transducer 14 and a data analysis device 31. Data analysis device 31 includes a control module 28, a communication module 30, an analysis module 32, a database module 34, an A/D converter module 35, and an interface module 36. System 27 also includes a pulser/receiver 37 electrically connected between ultrasonic transducer 14 and communication module 30.

Interface module 36 represents software and hardware necessary for interacting with a user, e.g., for receiving input from a user 42 and for outputting information to the user 42. Interface module 36 may receive input from input devices 40 and output data to output devices 38 that enable a user 42 to interact with data analysis device 12. For example, via interface module 36, user 42 may change operational parameters of data analysis device 12 and manipulate data stored in database module 34. Moreover, user 42 may interact with interface module 36 to initiate ultrasonic measurement of sample 16 to detect a defect 24 and, optionally, determine an approximate size and/or shape of defect 24. Further, user 42 may interact with data analysis device 12 to view and manipulate the acquired data via output devices 38 and input devices 40. During this process, interface module 36 may present a user 42 with user interface screens for interacting with analysis device 12, including, for example, the exemplary user interface screens shown in FIGS. 9-11. Exemplary input devices 40 include a keyboard, a touch screen, a mouse, a microphone, and the like. Output devices 38 may include, for example, an LCD screen, an LED array, a CRT screen, or a touch screen display.

Communication module 30 represents hardware and software necessary for communication between data analysis device 12 and another device, such as, for example, pulser/receiver 37, stage 26, or a device external to system 27, such as another computing device. The communication module 30 may include a single method or combination of methods to transfer data to and from data analysis device 12. Some methods may include a universal serial bus (USB) port, a PCI bus, or IEEE 1394 port for hardwire connectivity with high data transfer rates. In some examples, a storage device may be directly attached to one of these ports for data storage for post processing. The data may be pre-processed by control module 28 and/or analysis module 32 and ready for viewing, or the raw data may need to be completely processed before analyzing can begin.

Communication module 30 may also may include radio frequency (RF) communication or a local area network (LAN) connection. Moreover, communication may be achieved by direct connection or through a network access point, such as a hub or router, which may support wired or wireless communications.

Control module 28 represents control logic that, in response to input received from user 42 via interface module 36, directs the operation of data analysis device 12 and pulser/receiver 37. For example, control module 28 may comprise software instructions that, when executed, provide control logic for communicating commands to pulser/receiver 37 to commence ultrasonic measurement and data collection via ultrasonic transducer 14. Furthermore, control module 28 provides control logic for storing the collected ultrasonic or transformed (FFT) data within database module 34, and for invoking analysis module 32 to process the data automatically or in response to commands from user 42.

In response to a command from a user 42, control module 28 may instruct via communication module 30 at least one of stage 26 (FIG. 1) and ultrasonic transducer 14 (FIG. 1) to position sample 16 relative to transducer 14. As described above, at least one of stage 26 and ultrasonic transducer 14 may be translatable in at least one dimension. In some examples, control module 28 may cause stage 26 and ultrasonic transducer 14 to operate in conjunction to position sample 16 relative to transducer 14.

Once control module 28 has caused ultrasonic transducer 14 to be positioned relative to sample 16 such that transducer 14 contacts a first surface 22 of sample 16 either directly or via an interface fluid, control module 28 may control pulser/receiver 37 to generate an electrical pulse or waveform that is transmitted to the waveform generator in ultrasonic transducer 14 to generate an ultrasonic waveform 18. Ultrasonic transducer 14 directs at least a portion of ultrasonic waveform 18 into sample 16 through first surface 22, and ultrasonic waveform 18 may propagate through sample 16 is a direction substantially normal to first surface 22. Ultrasonic waveform 18 may comprise any suitable frequency, such as, for example, frequency between approximately 2.5 megahertz (MHz) and approximately 15 MHz. In some examples, waveform 18 may comprise a frequency of approximately 5 MHz. In some examples, the frequency of ultrasonic waveform 18 may influence the depth to which sample 16 is interrogated.

In some examples, a frequency and amplitude of ultrasonic waveform 18 may be stored in database module 34. Database module 34 represents hardware and software necessary for storing and retrieving data, and may comprise, for example, a suitable magnetic media, optical media, random access memory (RAM), read-only memory (ROM), non-volatile random access memory (NVRAM), electrically erasable programmable read-only memory (EEPROM), flash memory, or other media suitable for storing program code and data. In other examples, the frequency and, optionally, amplitude of ultrasonic waveform 18 may be input by user 42 via input devices 40.

Once generated by ultrasonic transducer 14 under control of pulser/receiver 37, ultrasonic waveform 18 propagates through sample 16 from first surface 22 toward second surface 23. In some examples, at least a portion of ultrasonic waveform 18 may resonate within defect 24. Defect 24 may include, for example, a feature than has a different acoustic impedance from surrounding material in sample 16. For example, defect 24 may be a void, a hole, a portion of sample 16 that has a different chemical composition or phase constitution, or another indication within sample 16, within which a portion of waveform 18 resonates to form resonated ultrasonic waveform 20. At least a portion of resonated ultrasonic waveform 20 propagates back through sample 16 to first surface 22.

At first surface 22, the ultrasonic waveform detector in ultrasonic transducer 14 senses resonated ultrasonic waveform 20. The waveform detector in ultrasonic transducer 14 may sense resonated ultrasonic waveform 20 as an analog signal (e.g., a piezoelectric detector generates an analog voltage in response to mechanical energy propagating through sample 16 as waveform 20), in which the amplitude and frequency of resonated ultrasonic waveform 20 is detected as a function of time. In other words, the data representative of resonated ultrasonic waveform 20 may be collected and/or stored as a function of time delay from first sensing resonated ultrasonic waveform 20.

In the example illustrated in FIG. 2, pulser/receiver 37 receives the analog signal from ultrasonic transducer 14 and communicates the analog signal to control module 28 via communication module 30. Control module 28 causes A/D converter module 35 to digitize the analog signal. As described above with respect to FIG. 1, the digital signal is representative of ultrasonic waveform data sensed by the waveform detector in ultrasonic transducer 14. The digital signal may comprise an array or matrix in which a first column or row stores sequential time values, a second column or row stores sequential amplitudes values associated with the respective time values, and a third column or row stores sequential frequency values associated with the respective time values. The granularity (e.g., the resolution of time values or spacing between adjacent time values) of the digital signal may be predetermined and stored in a memory of data analysis device 12, or may be input by a user. The granularity is controlled by the sampling rate at which A/D converter module 35 samples the analog signal when converting the analog signal to a digital signal. The sampling rate may be equal to or greater than the Nyquist rate. The precise sampling rate used may be selected based on considerations of the accuracy desired and data storage or processing limitations. In some examples, the sampling rate may be significantly higher than the Nyquist rate, such as, for example 1 gigahertz (GHz).

Similarly, the A/D converter module 35 may operate at a specific bit depth, which refers to the number of bits used to represent the amplitude of signal at a given time value. A greater bit depth may result in greater fidelity between the digital signal and the analog signal produced by ultrasonic transducer 14. However, a greater bit depth may also result in greater data processing and storage requirements. In some examples, the bit depth at which A/D converter module 35 operates may be greater than or equal to 8 bits, for example, 8 bits, 10 bits, 12 bits, 14 bits, or 16 bits.

In some examples, control module 28 causes the digital signal to be stored in database module 34 for later manipulation or may communicate the digital signal to analysis module 32 for analysis according to one or more techniques described herein.

Analysis module 32 receives the digital signal from control module 28, processes the data according to at least one of the techniques described herein, and may detect a presence of defect 24 and, optionally, determine an approximate size and/or shape of defect 24, automatically or in response to an instruction received from user 42. Examples of techniques that analysis module 32 may implement to detect defect 24 and, optionally, determine an approximate size and/or shape of defect 24 are described above with respect to FIG. 1 and below with respect to FIGS. 4-8.

In some examples, control module 28 may perform one or more of the described techniques at a plurality of locations on upper surface 22 and/or another surface of sample 16. Control module 28 may then utilize the sensed data for each of the plurality of locations to generate a multi-dimensional, e.g., two-dimensional or three dimensional, representation of at least one characteristic of the crystallographic texture of sample 16. One such technique will be described below with respect to FIG. 5, although other techniques described herein may be adapted to be performed at a plurality of locations on upper surface 22 or another surface of sample 16.

FIG. 3 illustrates a functional block diagram of another example of a system 29 that may be used to perform an ultrasonic crystallographic texture measurement on a sample 16. System 29 is similar to system 27 described with reference to FIG. 2. However, in contrast to system 27 illustrated in FIG. 2, data analysis device 33 of system 29 does not include an A/D converter module 35. Instead, system 29 includes an integrated pulser/receiver and A/D converter 39 connected between communication module 30 of data analysis device 33 ultrasonic transducer 14.

Modules having similar reference numerals in FIGS. 2 and 3 may perform similar functions and may comprise similar hardware, firmware, software, or combinations thereof. For example, interface module 36 represents software and hardware for interacting with a user. Communication module 30, database module 34 and analysis module 32 may also function as described with respect to FIG. 2

Similar to the functions with respect to system 27 of FIG. 2, control module 28 may control integrated pulser/receiver and A/D converter 39 to generate an electrical pulse or waveform that is transmitted to the waveform generator in ultrasonic transducer 14 to generate an ultrasonic waveform 18. Ultrasonic transducer 14 directs at least a portion of ultrasonic waveform 18 into sample 16 through first surface 22, and ultrasonic waveform 18 may propagate through sample 16 is a direction substantially normal to first surface 22. Ultrasonic waveform 18 may comprise any suitable frequency, such as, for example, frequency between approximately 2.5 megahertz (MHz) and approximately 15 MHz. In some examples, waveform 18 may comprise a frequency of approximately 5 MHz. In some examples, the frequency of ultrasonic waveform 18 may influence the depth to which sample 16 is interrogated.

Once generated by ultrasonic transducer 14 under control of integrated pulser/receiver and A/D converter 39, ultrasonic waveform 18 propagates through sample 16 from first surface 22 toward second surface 24. In some examples, at least a portion of ultrasonic waveform 18 may resonate within defect 24. Defect 24 may include, for example, a feature than has a different acoustic impedance from surrounding material in sample 16. For example, defect 24 may be a void, a hole, or a portion of sample 16 that has a different chemical composition or phase constitution, within which a portion of waveform 18 resonates to form resonated ultrasonic waveform 20. At least a portion of resonated ultrasonic waveform 20 propagates back through sample 16 to first surface 22.

At first surface 22, the ultrasonic waveform detector in ultrasonic transducer 14 senses resonated ultrasonic waveform 20. The waveform detector in ultrasonic transducer 14 may sense resonated ultrasonic waveform 20 as an analog signal (e.g., a piezoelectric detector generates an analog voltage in response to mechanical energy propagating through sample 16 as waveform 20), in which the amplitude and frequency of resonated ultrasonic waveform 20 is detected as a function of time. In other words, the data representative of resonated ultrasonic waveform 20 may be collected and/or stored as a function of time delay from first sensing resonated ultrasonic waveform 20.

In the example illustrated in FIG. 3, integrated pulser/receiver and A/D converter 39 receives the analog signal from ultrasonic transducer 14 and the A/D converter converts the analog signal to a digital signal before communicating the digital signal to control module 28 via communication module 30. Control module 28 then may cause analysis module 32 to perform one or more of the techniques described herein on the digital signal or may cause the digital signal to be stored in database module 34 for later manipulation and analysis.

Figure 4:
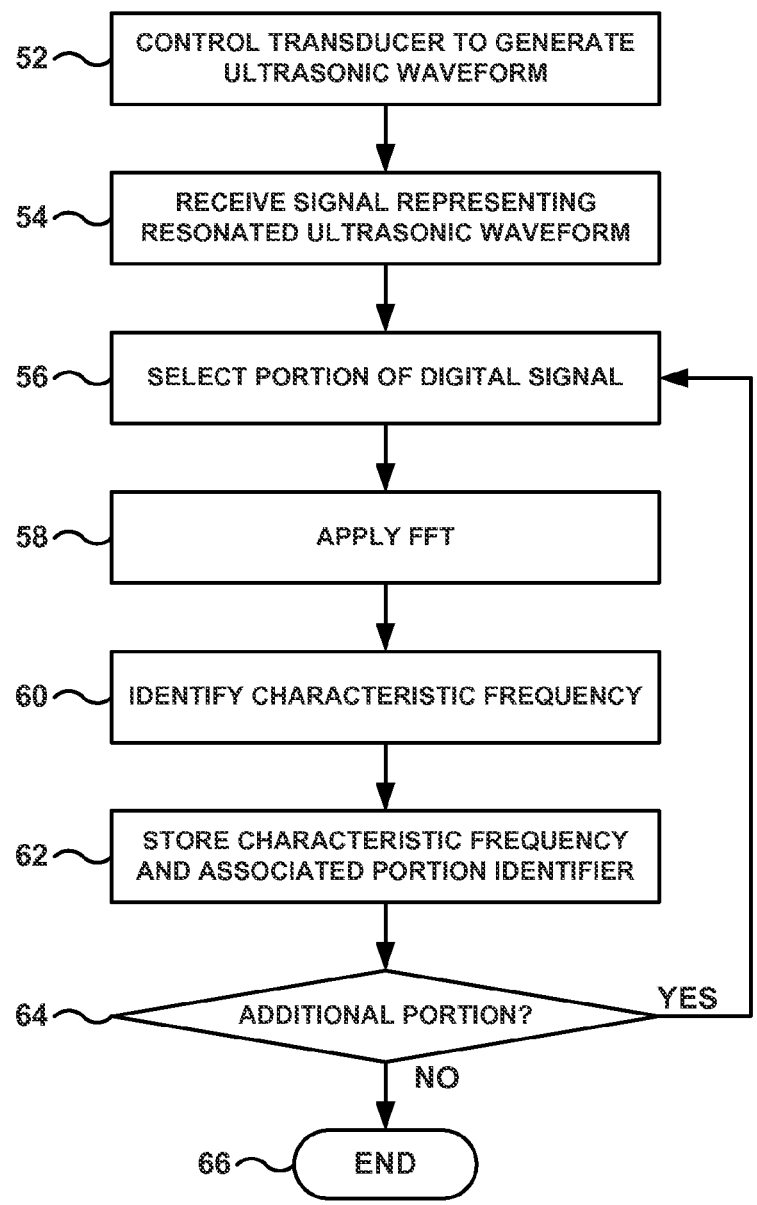
FIG. 4 is a flow diagram of an example technique for performing an ultrasonic measurement to detect a defect within a material.

FIG. 4 is a flow diagram of an example of a technique which data analysis device 33 (or data analysis device 12 or 31) may perform to determine a characteristic frequency of a portion of ultrasonic data, which may in turn be used to detect a defect 24 within a sample 16 and, optionally, determine an approximate size and/or shape of defect 24. FIG. 4 will be described with concurrent reference to FIG. 3, although other systems, such as system 27 illustrated in FIG. 2 or system 10 illustrated in FIG. 1, may be adapted to perform the technique illustrated in FIG. 4.

Initially, control module 28 causes integrated pulser/receiver and A/D converter 39 to generate a pulse or waveform that causes a waveform generator in ultrasonic transducer 14 to generate an ultrasonic waveform 18 (52). As described above, ultrasonic transducer 14 transmits ultrasonic waveform 18 into upper surface 22, either through direct contact or through an interface fluid, which may be utilized to ensure sufficient acoustic coupling between transducer 14 and upper surface 22.

Control module 28 may cause the ultrasonic generator to generate ultrasonic waveform 18 with substantially any frequency. In some examples, the frequency may be between approximately 2.5 MHz and 15 MHz. For example, the ultrasonic generator may generate ultrasonic waveform 18 with a frequency of approximately 5 MHz. The frequency of ultrasonic waveform 18 may influence the depth to which sample 16 is interrogated.

Ultrasonic waveform 18 propagates through sample 16 from first surface 22 toward second surface 24. In some examples, at least a portion of ultrasonic waveform 18 may encounter defect 24 and resonate within defect 24. Defect 24 may include, for example, a feature than has a different acoustic impedance from surrounding material in sample 16. For example, defect 24 may be a void, a hole, or a portion of sample 16 that has a different chemical composition or phase constitution, in which a portion of waveform 18 resonates to form resonated ultrasonic waveform 20. At least a portion of resonated ultrasonic waveform 20 propagates back through sample 16 to first surface 22.

At first surface 22, the ultrasonic waveform detector in ultrasonic transducer 14 senses resonated ultrasonic waveform 20. For example, as described above, the ultrasonic detector may comprise a piezoelectric crystal that generates a voltage when subjected to vibration, such as vibrations from reflected waveform 20. The waveform detector in ultrasonic transducer 14 may sense resonated ultrasonic waveform 20 as an analog signal (e.g., a piezoelectric detector generates an analog voltage in response to mechanical energy propagating through sample 16 as waveform 20), in which the amplitude and frequency of resonated ultrasonic waveform 20 is detected as a function of time. In other words, the data representative of resonated ultrasonic waveform 20 may be collected and/or stored as a function of time delay from first sensing resonated ultrasonic waveform 20.

Integrated pulser/receiver and A/D converter 39 converts the analog signal representative of the sensed reflected ultrasonic waveform 20 into a digital signal, which is then transmitted to control module 28 of data analysis device 33 via communication module 30. In other examples, as illustrated in FIG. 2, pulser/receiver 37 may transmit the analog signal via communication module 30 to A/D converter 35, which then may digitize the analog signal. In either case, control module 28 receives a signal representative of reflected ultrasonic waveform 20 (54).

The digital signal may comprise an array or matrix in which time values are stored in a first column or row. Corresponding amplitudes and frequencies are stored in additional columns or rows, respectively. Stated another way, the digital signal comprises a dataset $D(t_j, A_j, f_j)$, where $t_j$ are time values, $A_j$ are amplitude values, and $f_j$ are frequency values. Subscript j runs from 0 to n, where n is the number of time values for the complete dataset.

Control module 28 may transmit the digital signal to analysis module 32 to manipulate the digital signal and determine a characteristic frequency of one or more selected portions of the digital signal. Analysis module 32 may first select a portion of the digital signal (56) by selecting a subset of time values and associated amplitude values and frequency values. For example, analysis module 32 may select a plurality of time values $t_j$, where j=p, p+1, p+2, ..., q-2, q-1, q; and p and q are integers, each less than or equal to n. Time values $t_p$ and $t_q$ represent the initial and final times, respectively, for the selected portion. Analogously, $t_p$ and $t_q$ represent, respectively, the initial and final depths within sample 16 for the selected portion. Analysis module 32 also selects the corresponding amplitudes, $A_j$, and frequencies, $f_j$, where j=p, p+1, p+2, ..., q-2, q-1, q; and p and q are integers, each less than or equal to n. The number of time values (q-p+1) the analysis module 32 selects for the portion of the digital signal may depend on, for example, the desired resolution of the portion, e.g., the size of the portion, the time between adjacent time values, or the like. An increased number of time values in a selected portion of the digital signal may lead to reduced computation time, as fewer portions may be required to span the depth D of sample 16. However, an increased number of time values in a selected portion of the digital signal may also decrease the resolution of the portions, and may obscure features (e.g., defect 24) having a size less than the distance represented by the difference between the first time value (p) and the last time value (q) in the selected portion. In some examples, the number of time values in a portion may be selected to be representative of a length less than an expected size of defect 24, to increase the probability that the selected portion provides information for a single defect 24 in sample 16.

Once analysis module 32 has selected a portion of the digital signal, analysis module applies a Fast Fourier Transform (FFT) to the selected portion to convert the portion from the time domain to the frequency domain (58). When transformed into the frequency domain, the selected portion may include a characteristic frequency, which may be a dominant, central frequency or another harmonic frequency. Analysis module 32 may automatically identify the characteristic frequency (60), or may output the digital signal transformed into the frequency domain, enabling a user 42 to manually identify the dominant frequency (60).

Control module 28 may then cause the determined characteristic frequency and an identifier of the associated portion of the digital signal to be stored in database module 34 (62). In some examples, the identifier of the associated portion may be a first time value for the portion ($t_p$), a last time value for the portion ($t_q$), a median or mean time value for the portion, or another alphanumeric value that uniquely identifies the portion.

As illustrated in FIG. 4, the technique may be repeated by data analysis device 12 for each of a plurality of portions of the digital signal. For example, analysis module 32 may determine whether another portion of the digital signal remains to be analyzed (64), and if so (the "YES" branch of decision block 64), analysis module 32 select a second portion of the digital signal (56). The second portion of the digital signal may include a plurality of $t_j$ values and corresponding $A_j$ and $f_j$ values, in which j=q+1, q+2, ..., q+(r-1), m+r, where m and p are integers and m+p is less than or equal to n. In such an example, the first portion, where j=p, p+1, p+2, ..., q-2, q-1, q; and the second portion, where j=q+1, q+2, ..., q+(r-1), q+r; are substantially contiguous with each other, and represent positions within sample 16 that are directly adjacent each other.

In other examples, analysis module 32 may select a second portion of the digital signal that is not substantially contiguous with the first portion of the digital signal (56), e.g., the second portion may include a plurality of $t_j$ values in which j=q+10, q+11, ..., q+(r-1), q+r. In such an example, a time (e.g., position/depth) gap exists between the first portion and the second portion.

In either example, analysis module 32 may apply an FFT to the second portion to convert the data of the second portion from the time domain to the frequency domain (58) and identify a characteristic frequency of the portion (60). Control module 28 may then cause the determined characteristic frequency and an identifier of the second portion of the digital signal to be stored in database module 34 (62). Control module 28 may continue to iterate this technique until control module 28 or analysis module 32 determines that there are no remaining portions of the digital signal to analyze (the "NO" branch of decision block 64), at which point control module 28 or analysis module 32 ends the technique (66). The plurality of portions may combine to provide information about the nature of sample 16 (e.g., a presence or absence of defect 24) along a path traversed by ultrasonic waveform 18 and resonated ultrasonic waveform 20. A resolution of the information about the nature of sample 16 along the path may be influenced by, for example, the time width of each of the portions, the spacing of the portions, or the like. For example, a smaller time width (e.g., fewer time measurement points) for each individual portion may result in finer resolution of the crystallographic orientation information along the path. Conversely, a greater time width (e.g., more time measurement points) for each individual portion may result in finer resolution of the information about the nature of sample 16 along the path.

Figure 5:
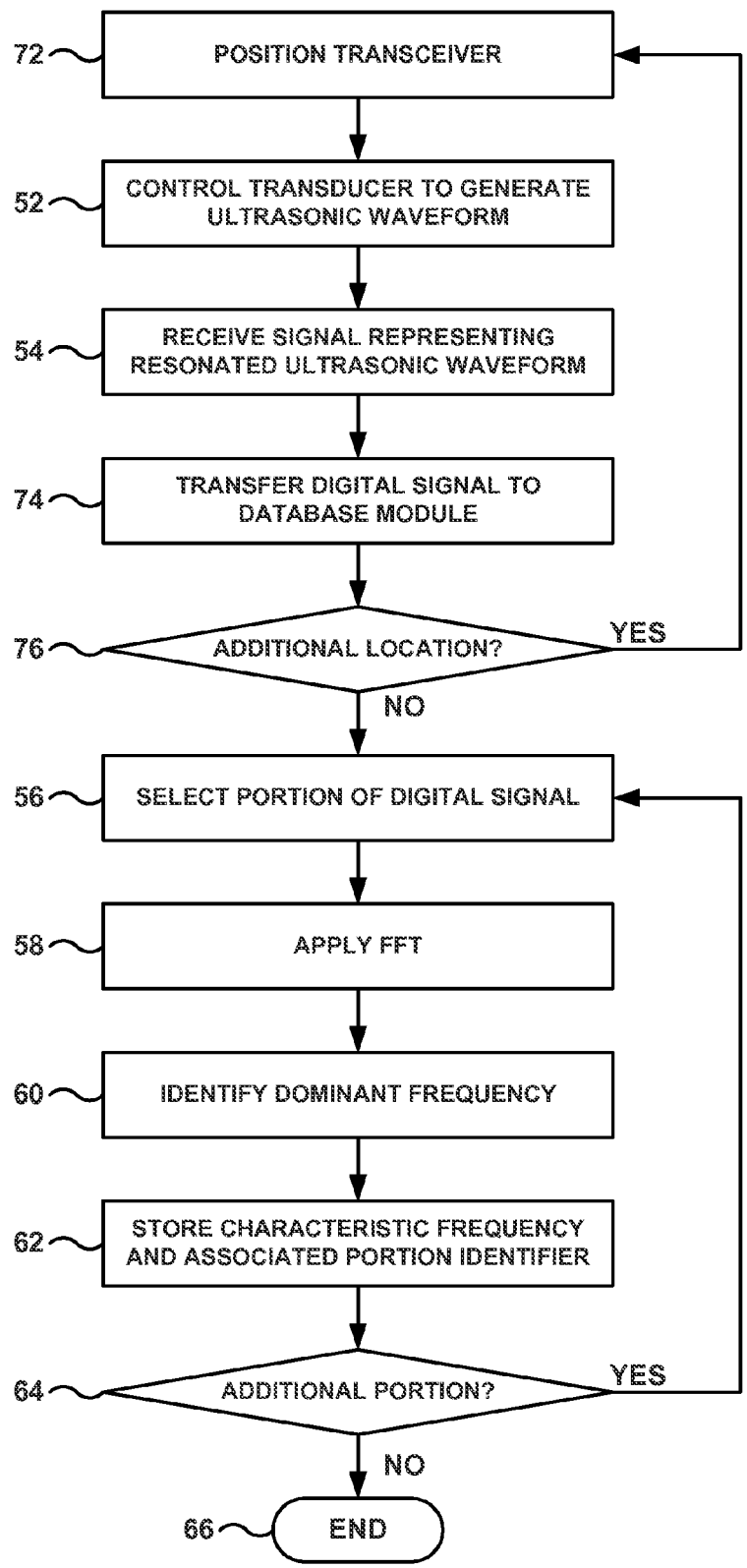
FIG. 5 is a flow diagram of another example technique for performing an ultrasonic measurement to detect a defect within a material.

As described briefly above, in some examples, control module 28 may cause ultrasonic waveform measurements to be performed at a plurality of positions along first surface 22 and/or another surface of sample 16. FIG. 5 illustrates one example of such a technique. FIG. 5 will be described with concurrent reference to system 29 of FIG. 3, although other systems, such as system 27 illustrated in FIG. 2 or system 10 illustrated in FIG. 1, may be adapted to perform the technique illustrated in FIG. 5.

Initially, control module 28 controls at least one of ultrasonic transducer 14 and stage 26 to position transducer 14 at a position on upper surface 22 (72). In some examples, stage 26 may be translatable in at least one dimension, and control module 28 may control stage 26 alone to position transducer 14 at a position on upper surface 22. In other examples, stage 26 may be substantially fixed in position and control module 28 may control the position of ultrasonic transducer 14 to position transducer 14 at a position on upper surface 22.

In some examples, control module 28 may control both stage 26 and ultrasonic transducer 14 in conjunction to position sample 16 relative to transducer 14. For example, stage 26 may be translatable in at least two dimensions (e.g., an x-y plane in the coordinate system shown in FIG. 1) and ultrasonic transducer 14 may be translatable in at least one dimension (e.g., the z-axis in FIG. 1). In other examples, each of ultrasonic transducer 14 and stage 26 may be translatable in three dimensions and control module 28 may control transducer 14 and stage 26 in conjunction to position transducer 14 relative to sample 16. For example, stage 26 may provide relatively coarse positioning of sample 16, while ultrasonic transducer 14 provides relatively more precise positioning. As another example, stage 26 may provide relatively slow positioning of sample 16 relative to transducer 14, while transducer 14 provides relatively faster positioning with respect to sample 16. In some examples, control module 28 may control one or both of ultrasonic transducer 14 or stage 26 to move according to another coordinate system. For example, control module 28 may control one or both of ultrasonic transducer 14 or stage 26 to be positioned according to a polar coordinate system or a spherical coordinate system. In other words, positioning of one or both of ultrasonic transducer 14 or stage 26 by control module 28 may include rotational positioning and not only linear positioning.

In some examples, a geometry of sample 16 (e.g., the geometry of first surface 22, second surface 24, and other surfaces of sample 16) may be collected by data analysis device 12 or programmed into data analysis device 12 by user 42. For example, a geometry of sample 16 may be represented by a numerical model, which may be stored in database module 34 or programmed by user 42 into data analysis device 12. The numerical model may describe a shape of surfaces of sample 16, and may also define a position of sample 16 relative to, for example, stage 26. Control module 28 may utilize the numerical model to position ultrasonic transducer 14 relative to first surface 22 or another surface of sample 16. Additionally and optionally, control module 28 may cause the position of ultrasonic transducer 14 relative to sample 16 and/or the orientation of transducer 14 relative to sample 16 to be stored in database module 34 and associated with the digital signal collected at this position. Such association of the position and/or orientation of transducer 14 with the digital signal may be used by control module 28 at a later time to construct a model of a characteristic of a crystallographic texture of sample 16 as a function of position within sample 16.

In some examples, instead of utilizing a single ultrasonic transducer 14, system 29 may include a plurality of ultrasonic transducers 14 which control module 28 controls to substantially simultaneously scan sample 16 at a corresponding plurality of locations. The location of each of the plurality of ultrasonic transducers 14 may be registered to the position of sample 16, and control module 28 may be configured to convolve the data received from two or more of the transducers 14 into a multidimensional data display format, or may allow a user to view data from each of the transducers 14 independently.

Once ultrasonic transducer 14 is positioned at a position on upper surface 22 or another surface of sample 16 (72), control module 28 then controls integrated pulser/receiver and A/D converter 39 to generate a pulse or waveform that causes the waveform generator in ultrasonic transducer 14 to generate an ultrasonic waveform 18 and transmit the waveform 18 into first surface 22 of sample 16 (52). At least a portion of ultrasonic waveform 18 propagates through sample 16 to defect 24, where at least a portion of waveform 18 resonates and propagates back through sample 16 as resonated waveform 20. When resonated waveform 20 reaches first surface 22, the waveform detector in ultrasonic transducer 14 detects resonated waveform 20 as a function of time delay, either from generation of waveform 18 or from initial sensing of reflected waveform 20. The waveform detector in transducer 14 detects reflected waveform 20 as an analog signal. Integrated pulser/receiver and A/D converter 39 may convert the analog signal representative of the sensed reflected ultrasonic waveform 20 into a digital signal, which is then transmitted to control module 28 of data analysis device 33 via communication module 30. In other examples, as illustrated in FIG. 2, pulser/receiver 37 may transmit the analog signal via communication module 30 to A/D converter 35, which then may digitize the analog signal. The digital signal may be stored in a data array or matrix with columns or rows of time, amplitude, and frequency, as described above.

In either case, control module 28 receives a digital signal representing reflected ultrasonic waveform 20 (54). In some examples, control module 28 then may transfer the digital signal to analysis module 32 for analysis, which will be described below. For purposes of the example shown in FIG. 5, control module 28 may transfer the digital signal to database module 34 (74) to store for later analysis by analysis module 32.

Once the control module 28 has transferred the collected digital signal to database module 34 for storage, control module 28 may determine whether an additional location of sample 16 is to be scanned (76). An additional location may be scanned for a variety of reasons. For example, a plurality of additional locations may be scanned in order to assemble a multi-dimensional (e.g., two-dimensional or three dimensional) representation of a presence or absence of defects 24 in sample 16. As another example, a user may desire information regarding a presence of defects 24 at two or more separate locations of sample 16.

When control module 28 determines that ultrasonic transducer 14 is to be moved to a different location relative to sample 16 (the "YES" branch of decision block 76), control module 28 may position transducer 14 at the new location (72). As described above, in some examples, the geometry of sample 16 (e.g., the geometry of first surface 22, second surface 24, and other surfaces of sample 16) may be collected by data analysis device 12 or programmed into data analysis device 12 by user 42. Control module 28 may utilize the geometry of sample 16 to position ultrasonic transducer 14 relative to first surface 22 or another surface of sample 16 at the new location. Additionally and optionally, control module 28 may cause the position of ultrasonic transducer 14 relative to sample 16 and/or the orientation of transducer 14 relative to sample 16 to be stored in database module 34 and associated with the digital signal collected at this position. Such association of the position and/or orientation of transducer 14 with the digital signal may be used by control module 28 at a later time to construct a model of a characteristic of a crystallographic texture of sample 16 as a function of position within sample 16.

Once control module 28 has caused ultrasonic transducer 14 to be positioned relative to sample 16 at the new position (72), control module 28 controls integrated pulser/receiver and A/D converter 39 to generate a pulse or waveform that causes a waveform generator in transducer 14 to generate an ultrasonic waveform 18 (52). The technique continues as described above, and control module 28 receives a signal representing reflected ultrasonic waveform 20 (54). Control module 28 then transfers the digital signal to database module 34 (74).

Control module 28 then determines whether ultrasonic transducer 14 is to be moved to an additional location relative to sample 16 and another ultrasonic scan performed (76). When control module 28 determines that ultrasonic transducer 14 is to be moved to an additional location, control module 28 causes transducer 14 to be positioned relative to sample 16 is a new position (72). The technique then continues as described above.

When control module 28 determines that ultrasonic transducer 14 is not to be moved to an additional location relative to sample 16 (the "NO" branch of decision block 76), control module 28 may proceed to control analysis of the collected digital signals by analysis module 32.

Under control of control module 28, analysis module 32 selects a portion of the digital signal (56) and applies an FFT to the digital signal (58) to transform the digital signal from the time domain to the frequency domain. Analysis module 32 then identifies the characteristic frequency for the selected portion of the digital signal (60). Control module 28 may then cause the determined characteristic frequency and an identifier of the associated portion of the digital signal to be stored in database module 34 (62).

Analysis module 32 then determines if an additional portion is to be selected and a crystallographic orientation value determined for the additional portion (64). In some examples, the number of iterations, or portions of the digital signal to be selected, may be stored in database module 34. In other examples, the number of portions of the digital signal to be selected and analyzed by analysis module 34 may be input by user 42 via input devices 40. In either case, analysis module 32 may determine that an additional portion of the digital signal is to be selected an analyzed, and may select a second portion of the digital signal (56). As described above, the second portion may include time values that are contiguous with the time values in the first portion (e.g., the first time value of the second portion may be one increment greater than the last time value of the first portion). In other examples, the second portion may include time values that are not contiguous with the time values in the first portion (e.g., the first time value of the second portion may be more than one increment greater than the last time value of the first portion).

Once analysis module 32 has selected the second portion of the digital signal (56), analysis module 32 may apply an FFT to the data in the second portion to transform the data from a time domain to a frequency domain (58). Analysis module 32 then identifies a characteristic frequency for the second portion from the transformed data (60). Control module 28 may then cause the determined characteristic frequency and an identifier of the second portion of the digital signal to be stored in database module 34 (62).

Analysis module 32 iterates this process of determining whether there are additional portions of the digital signal to be selected and analyzed (64) and analyzing the portion until module 32 determines that there are no remaining additional portions of the signal to be selected and analyzed (the "NO" branch of decision block 64). Analysis module 32 may perform this iterative technique to analyze the respective digital signal collected at each location on the surface of sample 16. Once the analysis of the digital signals is completed by analysis module 32, control module 28 may end the technique (66).

Figure 6:
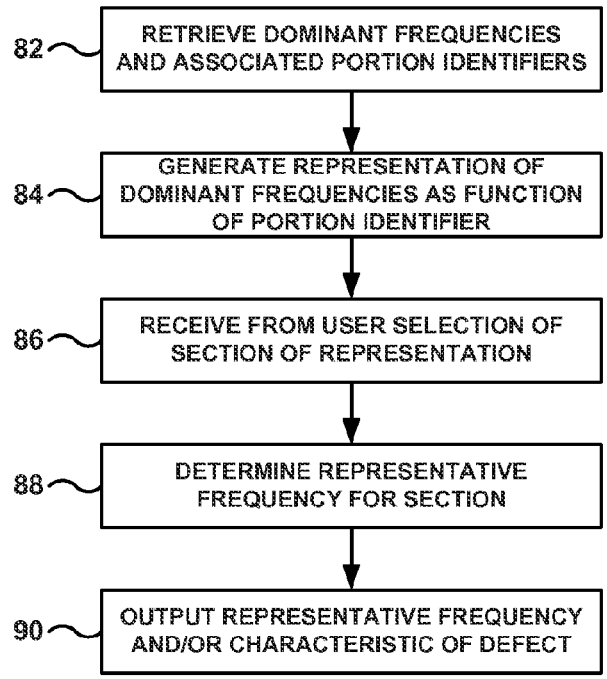
FIG. 6 is a flow diagram of an example technique for performing an ultrasonic measurement to measure a size and/or shape of a defect within a material.

FIG. 6 is a flow diagram that illustrates one example of a technique that data analysis device 12 may implement to determine a presence or an absence of a defect 24 in sample 16 based on the characteristic frequencies determined from the ultrasonic data and, optionally, to determine an approximate size and/or shape of a detected defect 24. FIG. 6 will be described with concurrent reference to system 29 of FIG. 3, although other systems, such as system 27 illustrated in FIG. 2 or system 10 illustrated in FIG. 1, may be adapted to perform the technique illustrated in FIG. 6.

In the example illustrated in FIG. 6, control module 28 may retrieve the dominant frequencies and associated portion indicators from database module 34 (82). Analysis module 32 may have previously determined the dominant frequencies for each portion via at least one of the techniques described above. The portion identifiers may include, for example, a first time value for the portion ($t_p$), a last time value for the portion ($t_q$), a median or mean time value for the portion, or another alphanumeric value that uniquely identifies the portion.

Figure 9:
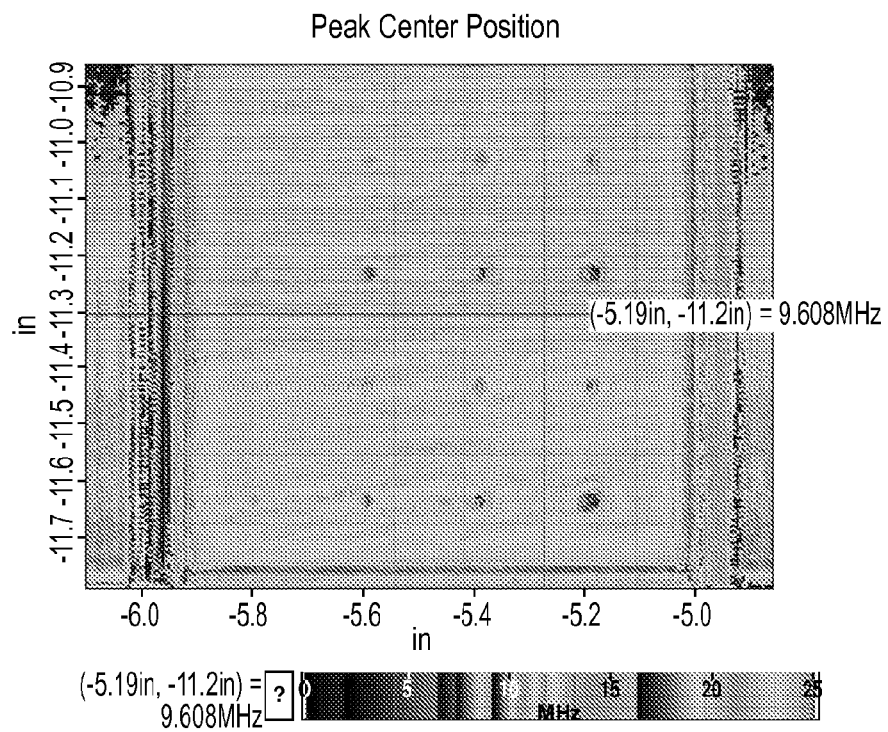
FIGS. 9-11 are example user interface screens from a computer implemented application for analyzing ultrasonic data.
Figure 10:
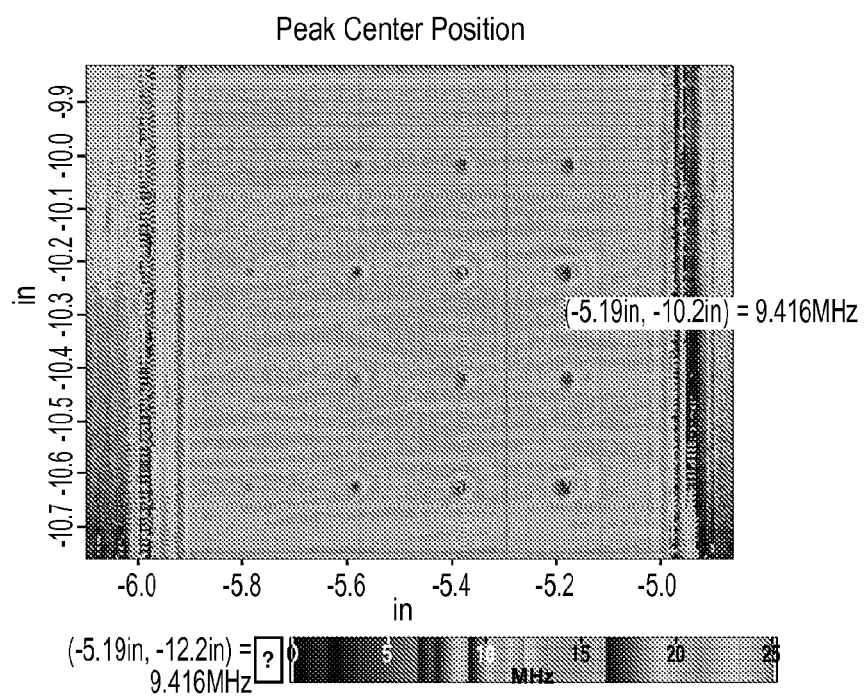
Figure 11:
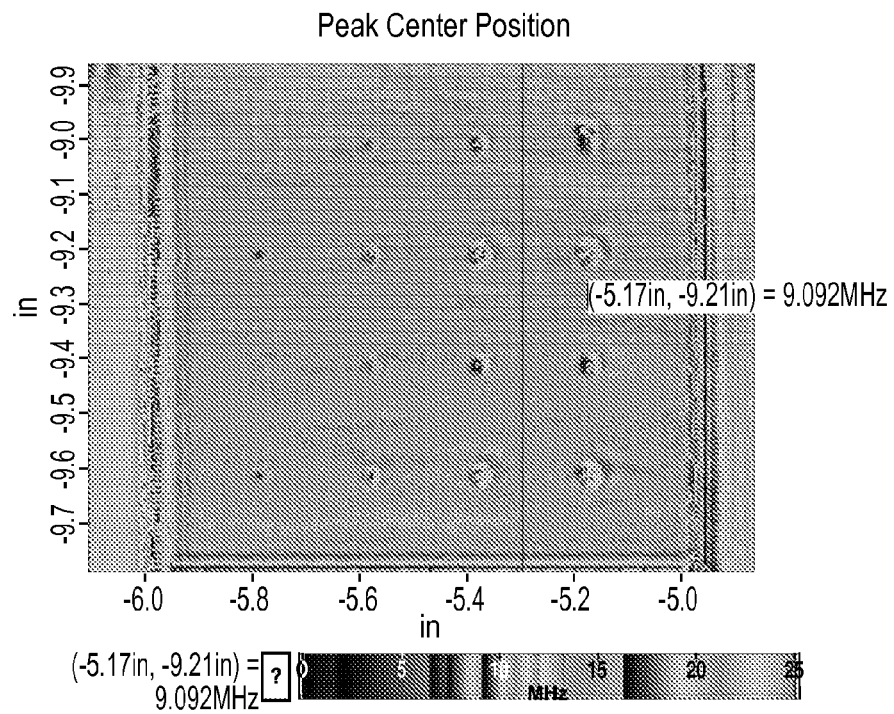

Once control module 28 has retrieved the dominant frequencies and associated portion indicators, control module 28 may generate a representation of the dominant frequency of each portion as a function of the portion and cause interface module 36 to output the representation via one or more output devices 38 (84). In various examples, control module 28 may generate the representation of the dominant frequencies as a function of portion indicator in table format, a bar or line graph, a false color map, or the like. In some examples, a false color map may provide a suitable format for the representation of the dominant frequencies. For example, control module 28 may generate a two-dimensional false color map in which the x- and y-dimensions represent location within sample 16 and the color of the locations within the false color map represent the characteristic frequency of the portion corresponding to that location. Control module 28 may utilize the false color map format when ultrasonic data has been collected at a plurality of locations of sample 16, such as when ultrasonic data has been collected along a two-dimensional plane or other surface of sample 16 or along three-dimensions of sample 16. FIGS. 9-11 illustrate examples of two-dimensional false color maps of characteristic frequencies as a function of portion.

In some examples in which control module 28 generates a three-dimensional false color map or another representation of three-dimensional data, control module 28 may cause interface module 36 to allow user 42 to manipulate the three-dimensional representation, e.g., rotate or change the viewpoint of the three-dimensional representation or select a plane within the three-dimensional representation. This may facilitate analysis of the data by user 42, e.g., to recognize sections of the representation that may indicate a defect 24.

Regardless of the format in which control module 28 generates the representation and interface module 36 causes output devices 38 to output the representation, user 42 may select a section of the representation that user 42 recognizes may indicate a defect 24 and control module 28 receives this selection (86). The section of the representation may include at least one portion and associated characteristic frequency. In some examples, user 42 may select at least two portions based on similarity between the characteristic frequencies of the at least two portions. For example, user 42 may determine that the characteristic frequencies of at least two portions that are near each other (e.g., adjacent to each other) are similar and the similarity suggests that the at least two portions are part of a single defect 24. For example, when the representation is a false color map, user 42 may interpret similar colors of at least two portions as representing a similar characteristic frequency and may infer that the similar characteristic frequency means that the at least two portions have a similar material composition. As another example, when the representation is a table of numerical values of the characteristic frequencies for each of the plurality of portions, user 42 may notice that at least two characteristic frequencies near each other in the table have approximately the same value, and may infer that the similar values indicate that the portions associated with the similar characteristic frequencies have a similar material composition.

User 42 may select the section (which includes at least one portion) in different ways. For example, when the representation is a false color map, user 42 may utilize an input device 42 such as a mouse to outline or shade the section user 42 wants to select. As another example, the user 42 may utilize an input device 42 to directly select at least one portion, e.g., by clicking on the portion in the false color map, clicking on the characteristic frequency when the frequencies are presented in a table form, or the like. User 42 may utilize any manner of indicating the section or selecting at least one portion.

When control module 28 receives the selection of the section of the representation from user 42 (86), control module 28 determines a representative characteristic frequency for the section (88). In examples in which the section includes only a single portion, the representative characteristic frequency for the section may be the characteristic frequency of the portion. However, when the section includes at least two portions, control module 28 may determine a representative characteristic frequency for the at least two portions. For example, control module 28 may determine a mean characteristic frequency for the section, a median characteristic frequency for the section, a mode of the characteristic frequencies of the at least two portions, or the like. The mean, median, or mode may then be the representative characteristic frequency for the section.

Control module 28 may then cause the representative characteristic frequency to be output by interface module 36 and/or may utilize the representative characteristic frequency to determine a characteristic of the defect 24 (90). In some examples, control module 28 may cause interface module 36 to output the representative characteristic frequency in a numerical form. Additionally and optionally, control module 28 may cause the interface module 36 to output further information regarding the representative characteristic frequency. The further information may include, for example, the mean, median, and/or mode of the characteristic frequencies when the section includes at least two portions or the values of the characteristic frequencies of each of the portions in the selected section.

As described above, control module 28 may utilize the representative characteristic frequency to determine an approximate size and/or an approximate shape of the detected defect 24. In some examples, control module 28 may control analysis module 32 to determine an approximate size of defect 24 based on the representative characteristic frequency and an equation that relates a frequency of a size of a resonator. As defect 24 causes waveform 18 to resonate, defect 24 may be considered to be a resonator, and the equation may approximate a size of defect 24.

In some examples, the equations may assume a certain shape of the resonator/defect 24. Thus, the equation may only provide an accurate size of defect 24 if defect 24 is approximately the shape for which the equation is valid. In some examples, the approximate shape of defect 24 may be known or anticipated, or the required accuracy for the calculation of the size of defect 24 may be low, so a single equation may be used by control module 28. For example, user 42 may know that defects of a certain approximate shape a predicted to form in sample 16, e.g., based on the composition of sample 16, the processing of sample 16, or the shape of sample 16. In some examples, user 42 may specify an equation for analysis module 32 to use, such as by inputting the equation or selecting the equation from a list of equations stored in a memory of data analysis device 33 (e.g., database module 34). In other examples, analysis module 32 may calculate an approximate size of defect 24 based on multiple equations, and control module 28 may output the resulting approximate sizes of defect 24 via interface module 36 and output devices 38 to present to user 42 a range of potential sizes of defect 24.

Equations 1 and 2 are two examples of equations that relate a resonance frequency of a resonator to a size of the resonator. Equation 1 relates the resonant frequency to a diameter for a sphere with a sound hole. In some examples, analysis module 32 may utilize Equation 1 to determine an approximate diameter of a defect 24 shaped like a flat-bottomed hole. Other equations may be used, for example, for defects 24 that are predicted to have a different shape or to present more possible sizes of defect 24 is the shape of defect 24 is unknown.

$$D = 17.87 \sqrt[3]{\frac{d}{f^2}} \qquad \text{Equation 1}$$

where D is the diameter of the sphere, d is the diameter of the sound hole, and f is the representative characteristic frequency. Equation 2 relates the resonant frequency to a diameter for a sphere with a necked sound hole. In some examples, control module 28 may utilize Equation 2 to determine an approximate diameter of a defect 24 shaped like a generally spherical hole that narrows on one end.

$$D = \sqrt[3]{\frac{3d^2 C^2}{8Lf^2\pi^2}} \qquad \text{Equation 2}$$

where D is the diameter of the sphere, d is the diameter of the sound hole, C is the speed of sound in the material from which the defect is formed, L is the length of the neck, and f is the representative characteristic frequency. Control module 28 may also use other equations, for example, for defects 24 that are predicted to have a different shape or to present more possible sizes of defect 24 is the shape of defect 24 is unknown.

In some examples, control module 28 may determine an approximate size and/or shape of defect 24 by comparing the representative characteristic frequency of section corresponding to defect 24 to a calibration curve constructed based on representative characteristic frequencies measured from defects of known sizes and shapes. In some examples, multiple calibration curves may be generated, one calibration curve for each shape of defect 24. In some examples, control module 28 and analysis module 32 may construct the calibration curve(s) based on data collected using data analysis device 33, while in other examples, the calibration curve(s) may be stored in database module 34 of data analysis device 33 or another memory of device 33.

Figure 8:
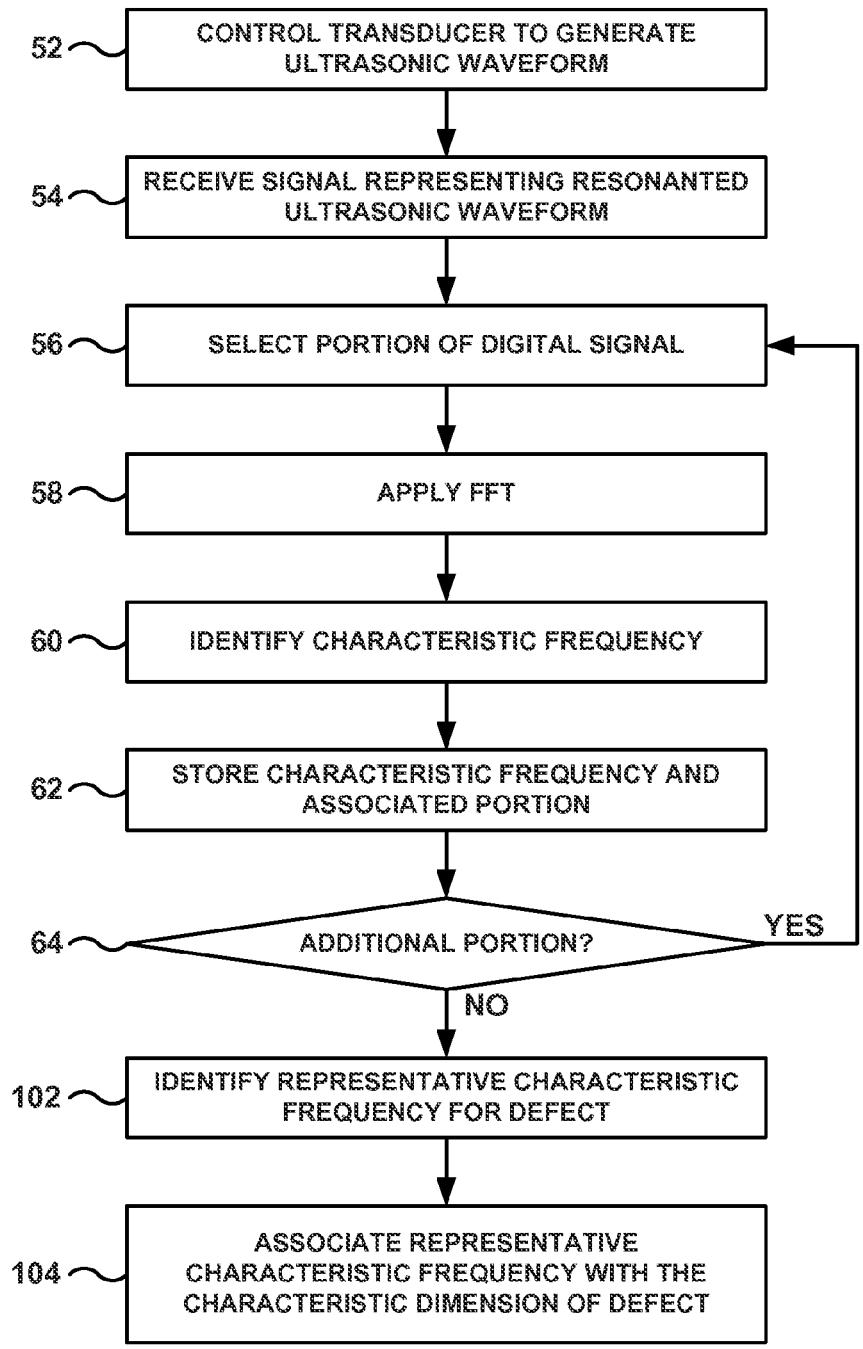
FIG. 8 is a flow diagram of an example technique for generating a calibration curve for use in measuring a size and/or shape of a defect within a material.

Analysis module 32 may determine the approximate size and shape of defect 24 by comparing the representative characteristic frequency of the section corresponding to defect 24 to each of the at least one calibration curves, determining which calibration curve best fits the representative characteristic frequency, and determining the approximate size of defect 24 from the calibration curve. FIG. 8, below, illustrates an example technique for constructing a calibration curve that analysis module 32 may utilize to determine an approximate size and/or shape of defect 24.

Regardless of how control module 28 and/or analysis module 32 determines the approximate size and/or shape of defect 24, once the approximate size and/or shape of defect 24 are determined, control module 28 may cause interface module 36 to output the approximate size and/or shape of defect 24 via output devices 38 (90). In some examples, when analysis module 32 determines a range of possible sizes and/or shapes of defect 24, control module 28 may cause interface module 36 to output the range of possible sizes and/or shapes of defect 24. Additionally or alternatively, control module 28 may cause interface module 36 to output the representative characteristic frequency of the section or other information described above with respect to the representative characteristic frequency (e.g., mean, median, and/or mode).

Figure 7:
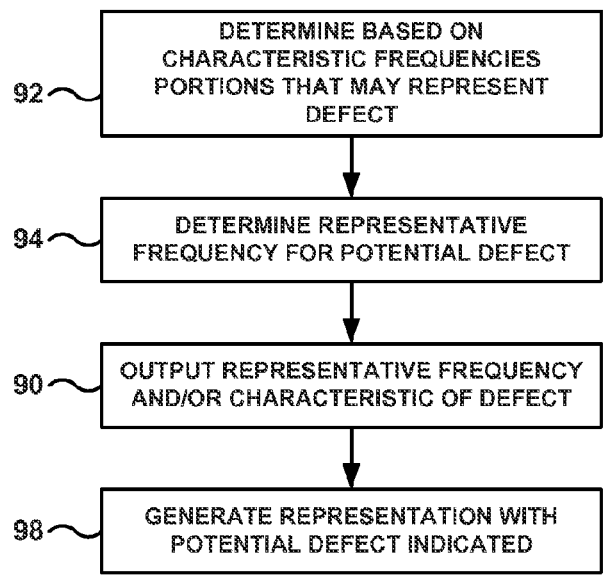
FIG. 7 is a flow diagram of another example technique for performing an ultrasonic measurement to measure a size and/or shape of a defect within a material.

FIG. 7 illustrates an example of a technique that control module 28 may implement to automatically, without intervention by user 42, determine an approximate size and/or shape of defect 24. FIG. 7 will be described with concurrent reference to system 29 of FIG. 3, although other systems, such as system 27 illustrated in FIG. 2 or system 10 illustrated in FIG. 1, may be adapted to perform the technique illustrated in FIG. 7.

Control module 28 may control analysis module 32 to determine characteristic frequencies and associated portions that may represent a defect 24 in sample 16 (92). Control module 28 may retrieve the characteristic frequencies and associated portion identifiers from database module 34 and communicate the characteristic frequencies and associated identifiers to analysis module 32. Alternatively, control module 28 may instruct analysis module 32 to analyze the characteristic frequencies to identify potential defects upon analysis module 32 determining the characteristic frequencies of the portions, e.g., based on the technique illustrated in FIG. 4 or FIG. 5.

Once analysis module 32 receives the data (characteristic frequencies and associated portion identifiers) and the instruction from control module 28 to analyze the characteristic frequencies, analysis module 32 may compare a first characteristic frequency to at least a second characteristic frequency to determine if the first characteristic frequency may indicate a defect 24. For example, analysis module 32 may determine a characteristic frequency or a range of characteristic frequencies that represent material with no defect based on a characteristic frequency or characteristic frequency range of a section of sample 16 (represented by one or more portions of the digital signal) that is known to not include a defect 24, such as a section of sample 16 that is near first surface 22. Analysis module 32 may then determine whether the selected portion indicates a presence of defect 24 or material with no defect 24 based on whether the characteristic frequency of the selected portion is similar to the characteristic frequency or characteristic frequency range of the section of sample 16 that is known to not include defect 24.

Conversely, in some examples analysis module 32 may determine a characteristic frequency or a range of characteristic frequencies that represent defect 24 based on a characteristic frequency or characteristic frequency range of a section of sample 16 (represented by one or more portions of the digital signal) or another material of similar chemical composition and phase constitution that is known to include defect 24. Analysis module 32 may then determine whether the selected portion indicates a presence of defect 24 or material with no defect 24 based on whether the characteristic frequency of the selected portion is similar to the characteristic frequency or characteristic frequency range of the section of sample 16 that is known to include defect 24. In some examples, analysis module 32 may compare the characteristic frequency of the selected portion to both a characteristic frequency or characteristic frequency range that is known to not indicate defect 24 and a characteristic frequency or characteristic frequency range that is known to indicate defect 24 and determine whether the characteristic frequency of the selected portion indicates a presence or absence of defect 24 based on both comparisons. In some examples, when analysis module 32 determines that the selected portion does not indicate the presence of defect 24, analysis module 32 selects another portion and compares the characteristic frequency of the selected portion to one or both of the characteristic frequencies or characteristic frequency ranges described above to determine whether the characteristic frequency of the selected portion indicates the presence or absence of defect 24. Analysis module 32 may continue this process until analysis module determines that a characteristic frequency of a selected portion indicates the presence of defect 24 or until module 32 has analyzed substantially all of the portions of data collected for sample 16.

In some examples, when analysis module 32 determines based on the above comparison(s) that the characteristic frequency of the selected portion indicates the presence of defect 24, analysis module 32 may analyze the characteristic frequency of at least one adjacent portion to determine if the adjacent portion indicates the presence of defect 24. In some implementations, the selected portion and the at least one adjacent portion may be sequential portions of the same digital signal, which may represent adjacent sections of sample 16. In other implementations, the selected portion and the at least one adjacent portion may be from two different digital signals, which control module 28 or analysis module 32 have determined represent adjacent sections of sample 16. For example, as illustrated in FIG. 5, control module 28 may cause ultrasonic transducer 14 to be positioned in at least two positions on first surface 22 of sample 16. As described above, control module 28 or analysis module 32 may determine an approximate depth within sample 16 that each portion represents based on the time values included in the portion and the approximate velocity of the ultrasonic waveform 18 and/or resonated waveform 20. Thus, control module 28 or analysis module 32 may concatenate the characteristic frequencies and associated portion identifiers of each of a plurality of digital signals (each collected at a separate location of first surface 22) to generate a two- or three-dimensional representation of characteristic signals within sample 16. Because of this, in some examples, the selected portion and the at least one adjacent portion that analysis module 32 compares in determining whether the selected portion may indicate defect 24 may be from different digital signals.

In analyzing the characteristic frequency of the at least one adjacent portion, analysis module 32 may perform at least one comparison. For example, analysis module 32 may analyze the characteristic frequency of the at least one adjacent portion as described above with respect to the selected portion, e.g., analysis module 32 may compare the characteristic frequency of the at least one adjacent portion to at least one of a characteristic frequency or characteristic frequency range that is known to not indicate defect 24 and a characteristic frequency or characteristic frequency range that is known to indicate defect 24. Analysis module 32 may determine whether the characteristic frequency of the at least one adjacent portion indicates a presence or absence of defect 24 based on the at least one comparison. When the at least one adjacent portion includes two or more adjacent portions, analysis module 32 may perform this comparison for each adjacent portion. Analysis module 32 then may group the portions that indicate the presence of defect 24 together as indicating the same defect 24.

In some examples, analysis module 32 may perform a comparison between the characteristic frequency of the selected portion and the characteristic frequency of the at least one adjacent portion. In comparing the characteristic frequency of the selected portion and the characteristic frequency of the at least one adjacent portion, analysis module 32 may determine a difference value between the characteristic frequencies. In examples in which analysis module 32 compares the characteristic frequency of the selected portion to a characteristic frequency of one adjacent portion, analysis module 32 may determine the difference value by subtracting the characteristic frequency of the selected portion from the characteristic frequency of the adjacent portion or by subtracting the characteristic frequency of the adjacent portion from the characteristic frequency of the selected portion.

In examples in which analysis module 32 compares the characteristic frequency of the selected portion to characteristic frequencies of at least two adjacent portion, analysis module 32 may determine a mean or median of the characteristic frequencies of the at least two adjacent portions. Analysis module 32 may then determine the difference value between the characteristic frequency of the selected portion and the mean characteristic frequency of the at least two adjacent portions by subtracting the characteristic frequency of the selected portion from the mean characteristic frequency or by subtracting the mean characteristic frequency from the characteristic frequency of the selected portion. In some examples, the use of a mean or median characteristic frequency may reduce the effect of noise in the digital signal on the detection of defect 24.

Regardless of the manner by which analysis module 32 determines the difference value, analysis module 32 may compare the difference value to a threshold value to determine whether the difference value indicates a transition from one type of material to a second type of material (e.g., from defect 24 to a non-defect or from a non-defect to defect 24). The threshold value may be selected based on an expected difference between a characteristic frequency of a first section of sample 16 that does not include defect 24 and a characteristic frequency of a second section of sample 16 that includes defect 24. When analysis module 32 determines the difference value is less than the threshold value, analysis module 32 may determine that the two characteristic frequencies indicate that the two portions of the digital signal represent a similar characteristic, e.g., both represent material with no defect 24 or both represent defect 24. In contrast, analysis module 32 determines the difference value is greater than the threshold value, analysis module 32 may determine that the two characteristic frequencies indicate that the two portions of the digital signal represent different characteristics, e.g., one represents material with no defect 24 and one represents defect 24.

Analysis module 32 may utilize at least one of the above comparisons to determine whether the at least one adjacent portion has a characteristic frequency that also indicates a presence of defect 24. When the characteristic frequency of the at least one adjacent portion indicates the presence of defect 24, analysis module 32 may interpret this to indicate that the selected portion and the at least one adjacent portion indicate the presence of the same defect 24. In this way, analysis module 32 may approximately determine which portions represent the same defect 24, and may generate an approximate representation of the portions and/or characteristic frequencies of the portions that represent the same defect for viewing by user 42.

In some implementations, analysis module 32 may determine a representative characteristic frequency of the portions analysis module 32 has determined indicate a single defect 24 (94). In some examples, analysis module 32 may determine that a single portion indicates defect 24 and adjacent portions indicate a different classification of material, e.g., a material with no defect 24. In some such examples, analysis module 32 may determine the representative characteristic frequency to be the characteristic frequency of the portion. In other examples, as described above, analysis module 32 may determine that the characteristic frequencies of at least two portions represent a single defect 24. In those situations, analysis module 32 may sometimes determine a representative characteristic frequency for all of the portions that indicate a single defect 24.

For example, as described with respect to FIG. 6, when the portions that indicate a single defect 24 include at least two portions, control module 28 may determine a representative characteristic frequency for the at least two portions. For example, control module 28 may determine a mean characteristic frequency for the at least two portions, a median characteristic frequency for the at least two portions, a mode of the characteristic frequencies of the at least two portions, or the like. The mean, median, or mode may then be the representative characteristic frequency for the at least two portions.

Control module 28 may then cause the representative characteristic frequency to be output by interface module 36 and/or may utilize the representative characteristic frequency to determine a characteristic of defect 24 (90). In some examples, control module 28 may cause interface module 36 to output the representative characteristic frequency in a numerical form. Additionally and optionally, control module 28 may cause the interface module 36 to output further information regarding the representative characteristic frequency. The further information may include, for example, the mean, median, and/or mode of the characteristic frequencies when the portions indicating defect 24 include at least two portions or the values of the characteristic frequencies of each of the portions.

In some examples, control module 28 may cause analysis module 32 to determine additional information about defect 24 based on the representative characteristic frequency. For example, as described above with respect to FIG. 6, analysis module 32 may determine an approximate size of defect 24 based on an equation that relates the representative characteristic frequency to a size of defect 24 (a resonator). Two example equations are shown above as Equations 1 and 2. Analysis module 32 also may utilize additional or alternative equations that relate a resonant frequency to a size of defect 24, based on the assumed, predicted, or potential shape of defect 24, as described above.

In other examples, analysis module 32 may determine an approximate shape and approximate size of defect 24 by comparing the representative characteristic frequency to a calibration curve constructed based on representative characteristic frequencies measured from defects of known sizes and shapes. In some examples, multiple calibration curves may be generated, one calibration curve for each shape of defect 24. In some examples, control module 28 and/or analysis module 32 may construct the calibration curve(s) based on data collected using data analysis device 33, while in other examples, the calibration curve(s) may be stored in database module 34 of data analysis device 33 or another memory of device 33.

Analysis module 32 may determine the approximate size and shape of defect 24 by comparing the representative characteristic frequency of the section corresponding to defect 24 to each of the at least one calibration curves, determining which calibration curve best fits the representative characteristic frequency, and determining the approximate size of defect 24 from the calibration curve. FIG. 8, below, illustrates an example technique for constructing a calibration curve that analysis module 32 may utilize to determine an approximate size and/or shape of defect 24.

Regardless of how control module 28 and analysis module 32 determines the approximate size and/or shape of defect 24, when analysis module 32 determines the approximate size and/or shape of defect 24, control module 28 may cause interface module 36 to output the approximate size and/or shape of defect 24 via output devices 38 (90). In some examples, when analysis module 32 determines a range of possible sizes and/or shapes of defect 24, control module 28 may cause interface module 36 to output the range of possible sizes and/or shapes of defect 24. Additionally or alternatively, control module 28 may cause interface module 36 to output the representative characteristic frequency of the section or other information described above with respect to the representative characteristic frequency (e.g., mean, median, and/or mode).

In some examples, in addition or as an alternative to causing interface module 36 to output the representative characteristic frequency, approximate size of defect 24 and/or approximate shape of defect 24 (90), control module 28 may generate a representation of the characteristic frequencies of the portions as a function of the portion, along with a visual indication of the portions that control module 28 and/or analysis module 32 have identified as indicating a presence of a defect 24 (98). As described above with respect to box (84) of FIG. 6, the representation may take various forms. For example, control module 28 may generate the representation of the dominant frequencies as a function of portion indicator in table format, as a bar or line graph, as a false color map, or the like. In some examples, a false color map may provide a suitable format for the representation of the dominant frequencies. For example, control module 28 may generate a two-dimensional false color map in which the x- and y-dimensions represent location within sample 16 and the color of the locations within the false color map represent the characteristic frequency of the portion corresponding to that location. Control module 28 may utilize the false color map format when ultrasonic data has been collected at a plurality of locations of sample 16, such as when ultrasonic data has been collected along a two-dimensional plane or other surface of sample 16 or along three-dimensions of sample 16. FIGS. 9-11 illustrate examples of two-dimensional false color maps of characteristic frequencies as a function of portion.

In some examples in which control module 28 generates a three-dimensional false color map or another representation of three-dimensional data, control module 28 may cause interface module 36 to allow user 42 to manipulate the three-dimensional representation, e.g., rotate or change the viewpoint of the three-dimensional representation or select a plane within the three-dimensional representation. This may facilitate analysis of the data by user 42, e.g., to recognize sections of the representation that may indicate a defect 24.

In some implementations, when control module 28 generates the representation of the characteristic frequencies as a function of the portion, control module 28 may specify the portions that indicate defect 24 based on the different color assigned to the portions having different characteristic frequencies. In this way control module 28 may specify the portions that indicate defect 24 by the representation of the portions themselves.

In other implementations, control module 28 may specify the portions that indicate defect 24 using additional indications. For example, control module 28 may outline the portions that indicate defect 24 in a false color map. As another example, when control module 28 generates a table that represents the characteristic frequencies as a function of the portions or portion identifiers, control module 28 may cause the characteristic frequencies that represent defect 24 to be highlighted, outlined, or otherwise denoted in the table. In any case, by generating a representation with the portions specified that control module 28 has identified indicate defect 24, user 42 may view the results of the analysis and appraise the accuracy of the analysis.

FIG. 8 is a flow diagram of an example technique that control module 28 may implement to generate a calibration curve. FIG. 8 will be described with concurrent reference to system 29 of FIG. 3, although other systems, such as system 27 illustrated in FIG. 2 or system 10 illustrated in FIG. 1, may be adapted to perform the technique illustrated in FIG. 8.

Control module 28 controls integrated pulser/receiver and A/D converter 39 to generate a pulse or waveform that causes the waveform generator in ultrasonic transducer 14 to generate an ultrasonic waveform 18 and transmit the waveform 18 into first surface 22 of sample 16 (52). In the example of FIG. 8, sample 16 includes a chemical composition and phase constitution that is approximately known and is similar to the chemical composition and phase constitution of other samples that will be tested subsequently. Additionally, in the example of FIG. 8, sample 16 includes at least one defect 24 that has a size and shape that are approximately known. For example, the size and shape of defect 24 may have been determined based using another analysis technique, or sample 16 may have been manipulated in a predetermined manner to form defect 24.

At least a portion of ultrasonic waveform 18 propagates through sample 16 to defect 24, where at least a portion of waveform 18 resonates and propagates back through sample 16 as resonated waveform 20. When resonated waveform 20 reaches first surface 22, the waveform detector in ultrasonic transducer 14 detects resonated waveform 20 as a function of time delay, either from generation of waveform 18 or from initial sensing of reflected waveform 20. The waveform detector in transducer 14 detects reflected waveform 20 as an analog signal. Integrated pulser/receiver and A/D converter 39 may convert the analog signal representative of the sensed reflected ultrasonic waveform 20 into a digital signal, which is then transmitted to control module 28 of data analysis device 33 via communication module 30. In other examples, as illustrated in FIG. 2, pulser/receiver 37 may transmit the analog signal via communication module 30 to A/D converter 35, which then may digitize the analog signal. The digital signal may be stored in a data array or matrix with columns or rows of time, amplitude, and frequency, as described above.

In either case, control module 28 receives a digital signal representing reflected ultrasonic waveform 20 (54). Control module 28 then transfers the digital signal to analysis module 32 for analysis. Under control of control module 28, analysis module 32 selects a portion of the digital signal (56) and applies an FFT to the digital signal (58) to transform the digital signal from the time domain to the frequency domain. Analysis module 32 then identifies the characteristic frequency for the selected portion of the digital signal (60). Control module 28 may then cause the determined characteristic frequency and an identifier of the associated portion of the digital signal to be stored in database module 34 (62).

Analysis module 32 then determines if an additional portion is to be selected and a crystallographic orientation value determined for the additional portion (64). In some examples, the number of iterations, or portions of the digital signal to be selected, may be stored in database module 34. In other examples, the number of portions of the digital signal to be selected and analyzed by analysis module 34 may be input by user 42 via input devices 40. In either case, analysis module 32 may determine that an additional portion of the digital signal is to be selected an analyzed, and may select a second portion of the digital signal (56). As described above, the second portion may include time values that are contiguous with the time values in the first portion (e.g., the first time value of the second portion may be one increment greater than the last time value of the first portion). In other examples, the second portion may include time values that are not contiguous with the time values in the first portion (e.g., the first time value of the second portion may be more than one increment greater than the last time value of the first portion).

Once analysis module 32 has selected the second portion of the digital signal (56), analysis module 32 may apply an FFT to the data in the second portion to transform the data from a time domain to a frequency domain (58). Analysis module 32 then identifies a characteristic frequency for the second portion from the transformed data (60). Control module 28 may then cause the determined characteristic frequency and an identifier of the second portion of the digital signal to be stored in database module 34 (62).

Analysis module 32 iterates this process of determining whether there are additional portions of the digital signal to be selected and analyzed (64) and analyzing the portion until module 32 determines that there are no remaining additional portions of the signal to be selected and analyzed (the "NO" branch of decision block 64). Analysis module 32 may perform this iterative technique to analyze the respective digital signal collected at each location on the surface of sample 16.

Once the analysis module 32 has completed analysis of the digital signals, analysis module or control module 28 may identify a representative characteristic frequency for each of the at least one defects 24, which have known sizes and shapes (102). In some examples, to identify the representative characteristic frequency for each of the at least one defects 24 (102), control module 28 may generate a representation of the dominant frequencies as a function of portion identifier (84), receive from user 42 a selection of a section of the representation, which may include at least one portion (86), and determine a representative characteristic frequency for the section (88), as described above with respect to FIG. 6. In other examples, to identify the representative characteristic frequency for each of the at least one defects 24 (102), control module 28 may determine based on the characteristic frequencies portions that may represent defect 24 (92) and determine a representative characteristic frequency for the defect 24 (94), as described with respect to FIG. 7.

Once control module 28 has determined the representative characteristic frequency of the portions indicating defect 24 (102), control module 28 may associate the representative characteristic frequency with a known characteristic dimension of the defect 24 (104). For example, the characteristic dimension of defect 24 may be the diameter or volume of the defect 24. In some examples, the shape of defect 24 is also associated with the characteristic frequency and the characteristic dimension of defect 24.

Control module 28 may repeat the technique illustrated in FIG. 8 for a plurality of defects 24 of known size and shape within a single sample 16 and/or for a plurality of samples 16 having defects 24 of known sizes and shapes. Control module 28 then may assemble the data from the multiple defects 24 and/or multiple samples 16 to create a calibration curve.

Figure 12:
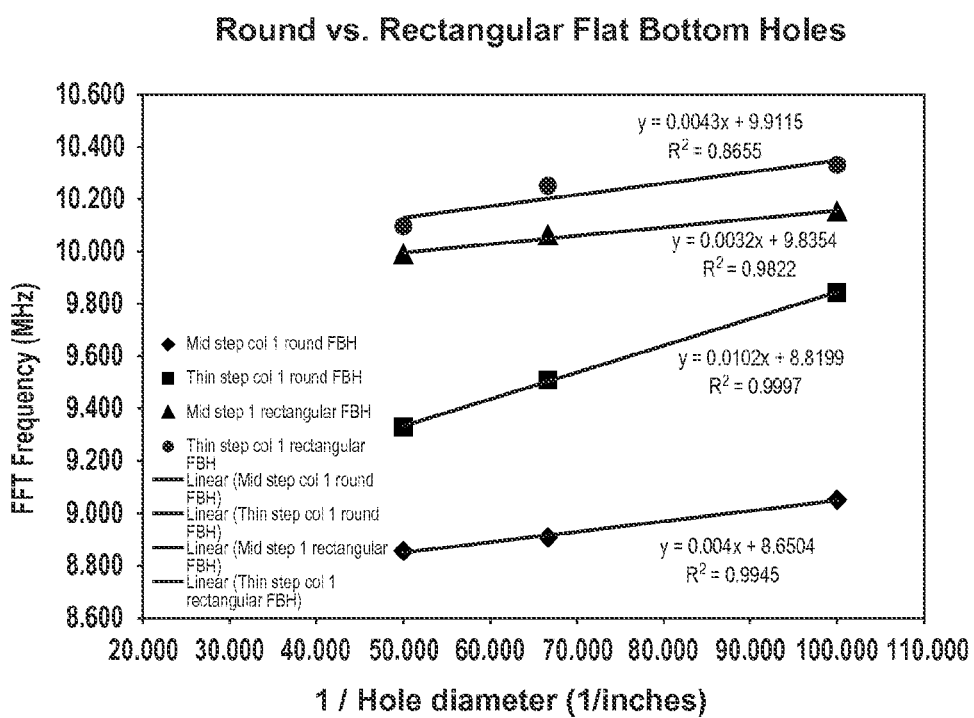
FIG. 12 is a plot of example calibration curves generated from the ultrasonic data shown in FIGS. 9-11.

In some examples, a separate calibration curve may be formed for each shape of defect 24. Additionally or alternatively, a separate calibration curve may be formed for each of a set of different dimensions of a defect 24. For example, for a defect 24 that is a flat-bottomed hole, a first calibration curve may be formed for the diameter of the sphere and a second calibration curve may be formed for at least one chord of the sphere. FIG. 12 illustrates examples of such calibration curves.

In some examples, in addition assembling the data from the multiple defects 24 and/or multiple samples 16 to create a calibration curve, control module 28 may determine an equation for the calibration curve, for example, using linear regression. As shown below in FIG. 12, an approximately linear relationship exists when the representative characteristic frequency is plotted versus the inverse of the hole diameter for a flat-bottomed hole defect. In some examples, control module 28 may use the determined calibration curve equation to estimate the size and/or shape of an unknown defect 24 in a subsequent sample 16.

The techniques described in this disclosure, including those attributed to data analysis device 12, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied a general purpose or purpose-built computing device. The term "processor" or "processing circuitry" may generally refer to any of the foregoing logic circuitry, alone or in combination with other logic circuitry, or any other equivalent circuitry.

Such hardware, software, firmware, or combinations thereof may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware and/or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), magnetoresistive random access memory (MRAM), FLASH memory, magnetic data storage media, optical data storage media, or the like. The instructions may be executed to support one or more aspects of the functionality described in this disclosure.

EXAMPLE

Transmission ultrasonic data collected from a step block containing round and rectangular flat bottom holes of various sizes. FIG. 9 is an image of some of the ultrasonic data collected on the thick section of the step block after transformation of the data using FFT. FIG. 10 is an image of some of the ultrasonic data collected on the mid-thickness section of the step block after transformation of the data using FFT. FIG. 11 is an image of some of the ultrasonic data collected on the thin section of the step block after transformation of the data using FFT.

FIG. 12 is a plot of FFT frequency versus inverse hole diameter for round and rectangular flat bottom holes. Each of the lines in FIG. 12 is a best-fit line calculated using linear regression based on the data points shown in FIG. 12. The data points are categorized by shape of the flat bottom hole and section of the block from which the data was collected. FIG. 12 illustrates that there is an approximately linear relationship between the FFT frequency of a defect and the inverse of the size of the defect. FIG. 12 also suggest that an approximate shape of the defect may be determined based on an FFT frequency of the defect, once a plurality of calibration curves have been generated for defects of different shapes, because different shapes may generate calibration curves that have a different slope and/or intercept.

Various examples have been described. These and other examples are within the scope of the following claims.

What is claimed is:

1. A system comprising:
a data analysis device configured to:
receive from an ultrasonic waveform detector ultrasonic waveform data representative of an ultrasonic waveform that propagated through a sample and resonated within a defect within the sample;
select a portion of the ultrasonic waveform data;
apply a Fast Fourier Transform to the portion of the ultrasonic waveform data to transform the portion from a time domain to a frequency domain;
identify a characteristic frequency of the portion in the frequency domain; and
determine a characteristic of the defect by at least one of (1) comparing the characteristic frequency to a calibration curve or (2) calculating an approximate size of the defect using at least one equation that relates the characteristic frequency to the approximate size of the defect.

2. The system of claim 1, wherein the data analysis device is configured to determine the characteristic of the defect by comparing the characteristic frequency to the calibration curve, and wherein the calibration curve comprises a plot of characteristic frequencies of defects of a known shape and known sizes versus an inverse of the known sizes.

3. The system of claim 1, wherein the data analysis device is configured to determine the characteristic of the defect by calculating the approximate size of the defect using at least one equation that relates the characteristic frequency to the approximate size of the defect, and wherein the at least one equation comprises the equation:

$$D = 17.87 \sqrt[3]{\frac{d}{f^2}}$$

wherein D is an approximate diameter of the defect, d is a diameter of a sound hole of the defect, and f is the characteristic frequency of the portion.

4. The system of claim 1, wherein the data analysis device is configured to determine the characteristic of the defect by calculating the approximate size of the defect using at least one equation that relates the characteristic frequency to the approximate size of the defect, and wherein the at least one equation comprises the equation:

$$D = \sqrt[3]{\frac{3d^2C^2}{8Lf^2\pi^2}}$$

wherein D is an approximate diameter of the defect, d is a diameter of a sound hole of the defect, C is a speed of sound, L is a length of a neck of the defect, and f is the characteristic frequency of the portion.

5. The system of claim 1, wherein the data analysis device is configured to determine the characteristic of the defect based on at least two equations that relate the characteristic frequency to a respective approximate size of the defect, and wherein the data analysis device is configured to output a range of approximate sizes based on the respective approximate sizes.

6. The system of claim 1, wherein the data analysis device is configured to:
select a first portion of the ultrasonic waveform data;
apply a Fast Fourier Transform to the first portion of the ultrasonic waveform data to transform the portion from a time domain to a frequency domain;
identify a first characteristic frequency of the first portion in the frequency domain;
select a second portion of the ultrasonic waveform data;
apply a Fast Fourier Transform to the second portion of the ultrasonic waveform data to transform the portion from a time domain to a frequency domain;
identify a second characteristic frequency of the second portion in the frequency domain; and
generate a representation of at least the first characteristic frequency and the second characteristic frequency as a function of the portion.

7. The system of claim 6, wherein the data analysis module is configured to:
receive an input from a user selecting at least one portion from the representation;

determine a representative characteristic frequency for the at least one portion; and determine the characteristic of the defect based on the representative characteristic frequency of the at least one portion.

8. A method comprising:

with one or more processors, receiving from an ultrasonic waveform detector ultrasonic waveform data representative of an ultrasonic waveform that propagated through a sample and resonated within a defect within the sample;

with the one or more processors, selecting a portion of the ultrasonic waveform data;

with the one or more processors, applying a Fast Fourier Transform to the portion of the ultrasonic waveform data to transform the portion from a time domain to a frequency domain;

with the one or more processors, identifying a characteristic frequency of the portion in the frequency domain; and with the one or more processors, determining a characteristic of the defect by at least one of (1) comparing the characteristic frequency to a calibration curve or (2) calculating an approximate size of the defect using at least one equation that relates the characteristic frequency to the approximate size of the defect.

9. The method of claim 8, wherein the calibration curve comprises a plot of characteristic frequencies of defects of a known shape and known sizes versus an inverse of the known sizes.

10. The method of claim 8, wherein determining the characteristic of the defect by at least one of (1) comparing the characteristic frequency to the calibration curve and (2) calculating the approximate size of the defect using at least one equation that relates the characteristic frequency to the approximate size of the defect comprises determining the characteristic of the defect based on:

$$D = 17.87 \sqrt[3]{\frac{d}{f^2}}$$

wherein D is an approximate diameter of the defect, d is a diameter of a sound hole of the defect, and f is the characteristic frequency of the portion.

11. The method of claim 8, wherein determining the characteristic of the defect by at least one of (1) comparing the characteristic frequency to the calibration curve and (2) calculating the approximate size of the defect using at least one equation that relates the characteristic frequency to the approximate size of the defect comprises determining the characteristic of the defect based on:

$$D = \sqrt[3]{\frac{3d^2C^2}{8Lf^2\pi^2}}$$

wherein D is an approximate diameter of the defect, d is a diameter of a sound hole of the defect, C is a speed of sound, L is a length of a neck of the defect, and f is the characteristic frequency of the portion.

12. The method of claim 8, wherein determining the characteristic of the defect by at least one of (1) comparing the characteristic frequency to a calibration curve and (2) calculating an approximate size of the defect using at least one equation that relates the characteristic frequency to the approximate size of the defect comprises determining the characteristic of the defect based on at least two equations that relate the characteristic frequency to an approximate size of the defect, further comprising outputting a range of approximate sizes based on the approximate sizes determined based on the at least two equations.

13. The method of claim 8, wherein:

selecting the portion of the ultrasonic waveform data comprises selecting a first portion of the ultrasonic waveform data;

applying the Fast Fourier Transform to the portion of the ultrasonic waveform data comprises applying a Fast Fourier Transform to the first portion of the ultrasonic waveform data to transform the portion from a time domain to a frequency domain;

identifying the characteristic frequency of the portion in the frequency domain comprises identify a first characteristic frequency of the first portion in the frequency domain; and wherein the method further comprises:

with the one or more processors, selecting a second portion of the ultrasonic waveform data;

with the one or more processors, applying a Fast Fourier Transform to the second portion of the ultrasonic waveform data to transform the portion from a time domain to a frequency domain;

with the one or more processors, identifying a second characteristic frequency of the second portion in the frequency domain; and with the one or more processors, generating a representation of at least the first characteristic frequency and the second characteristic frequency as a function of the portion.

14. The method of claim 13, further comprising:

with the one or more processors, receiving an input from a user selecting at least one portion from the representation;

with the one or more processors, determining a representative characteristic frequency for the at least one portion; and with the one or more processors, determining the characteristic of the defect based on the representative characteristic frequency of the at least one portion.

15. A non-transitory computer readable medium comprising instructions that cause a programmable processor to:

receive from an ultrasonic waveform detector ultrasonic waveform data representative of an ultrasonic waveform that propagated through a sample and resonated within a defect within the sample;

select a portion of the ultrasonic waveform data;

apply a Fast Fourier Transform to the portion of the ultrasonic waveform data to transform the portion from a time domain to a frequency domain;

identify a characteristic frequency of the portion in the frequency domain; and determine a characteristic of the defect by at least one of (1) comparing the characteristic frequency to a calibration curve or (2) calculating an approximate size of the defect using at least one equation that relates the characteristic frequency to the approximate size of the defect.

16. The non-transitory computer readable medium of claim 15, wherein the calibration curve comprises a plot of characteristic frequencies of defects of a known shape and known sizes versus an inverse of the known sizes.

17. The non-transitory computer readable medium of claim 15, wherein the instructions cause the programmable processor to:
- select a first portion of the ultrasonic waveform data;
- apply a Fast Fourier Transform to the first portion of the ultrasonic waveform data to transform the portion from a time domain to a frequency domain;
- identify a first characteristic frequency of the first portion in the frequency domain;
- select a second portion of the ultrasonic waveform data;
- apply a Fast Fourier Transform to the second portion of the ultrasonic waveform data to transform the portion from a time domain to a frequency domain;
- identify a second characteristic frequency of the second portion in the frequency domain; and
- generate a representation of at least the first characteristic frequency and the second characteristic frequency as a function of the portion.

18. The non-transitory computer readable medium of claim 17, wherein instructions cause the programmable processor to generate a false color map of the first characteristic frequency and the second characteristic frequency as a function of the portion.

19. The non-transitory computer readable medium of claim 18, further comprising instructions that cause the programmable processor to:
- receive an input from a user selecting at least one portion from the representation;
- determine a representative characteristic frequency for the at least one portion; and
- determine the characteristic of the defect based on the representative characteristic frequency of the at least one portion.

20. The non-transitory computer readable medium of claim 19, wherein the representative characteristic frequency comprises at least one of a mean of the characteristic frequencies of the at least one portion, a median of the characteristic frequencies of the at least one portion, or a mode of the characteristic frequencies of the at least one portion.

* * * * *